(12) United States Patent
Thorens et al.

(10) Patent No.: US 12,059,524 B2
(45) Date of Patent: Aug. 13, 2024

(54) SMOKING SYSTEM HAVING A LIQUID STORAGE PORTION

(71) Applicant: Philip Morris USA Inc., Richmond, VA (US)

(72) Inventors: Michel Thorens, Moudon (CH); Jean-Marc Flick, Pomy (CH); Olivier Yves Cochand, Dombresson (CH); Flavien Dubief, Neuchatel (CH)

(73) Assignee: PHILIP MORRIS USA INC., Richmond, VA (US)

( * ) Notice: Subject to any disclaimer, the term of this patent is extended or adjusted under 35 U.S.C. 154(b) by 985 days.

(21) Appl. No.: 16/915,185

(22) Filed: Jun. 29, 2020

(65) Prior Publication Data
US 2020/0323268 A1 Oct. 15, 2020

Related U.S. Application Data

(63) Continuation of application No. 15/220,927, filed on Jul. 27, 2016, now Pat. No. 11,013,265, which is a
(Continued)

(30) Foreign Application Priority Data

Oct. 27, 2009 (EP) .................................... 09252490

(51) Int. Cl.
*A24F 40/44* (2020.01)
*A24F 40/485* (2020.01)
(Continued)

(52) U.S. Cl.
CPC ............. *A61M 15/06* (2013.01); *A24F 40/44* (2020.01); *A24F 40/485* (2020.01);
(Continued)

(58) Field of Classification Search
None
See application file for complete search history.

(56) References Cited

U.S. PATENT DOCUMENTS 358,002 A 2/1887 Trauernicht
1,514,682 A 11/1924 Wilson
(Continued)

FOREIGN PATENT DOCUMENTS

BE 421623 A 6/1937
CA 1202378 A1 3/1986
(Continued)

OTHER PUBLICATIONS

English Translation of WO 97/48293, Masayuki et al (Year: 1997).*
(Continued)

*Primary Examiner* — Dionne W. Mayes
(74) *Attorney, Agent, or Firm* — Harness, Dickey & Pierce, P.L.C.

(57) ABSTRACT

A smoking system includes a capillary wick for holding liquid, at least one air inlet, at least one air outlet and a chamber between the air inlet and air outlet. The air inlet, the air outlet and the chamber are arranged so as to define an air flow route from the air inlet to the air outlet via the capillary wick so as to convey aerosol formed from the liquid to the air outlet. The smoking system further includes at least one guide for channeling the air flow in the air flow route, so as to control particle size in the aerosol. The smoking system optionally includes at least one heater for heating the liquid in at least a portion of the capillary wick to form the aerosol.

14 Claims, 13 Drawing Sheets

Related U.S. Application Data continuation of application No. 12/913,510, filed on Oct. 27, 2010, now Pat. No. 9,420,829.

(51) Int. Cl.
*A61M 11/04* (2006.01)
*A61M 15/06* (2006.01)
*H05B 1/02* (2006.01)
*H05B 3/00* (2006.01)
*A24F 40/10* (2020.01)
*A61M 11/00* (2006.01)
*A61M 16/00* (2006.01)

(52) U.S. Cl.
CPC ......... *A61M 11/042* (2014.02); *H05B 1/0202* (2013.01); *H05B 1/0244* (2013.01); *H05B 3/0014* (2013.01); *A24F 40/10* (2020.01); *A61M 11/002* (2014.02); *A61M 2016/0021* (2013.01); *A61M 2016/0039* (2013.01); *A61M 2205/3375* (2013.01); *A61M 2205/3653* (2013.01); *A61M 2205/8206* (2013.01); *A61M 2206/14* (2013.01); *A61M 2206/16* (2013.01)

(56) References Cited

U.S. PATENT DOCUMENTS

| | | |
|---|---|---|
| 1,771,366 A | 7/1930 | Wyss et al. |
| 1,968,509 A | 7/1934 | Tiffany |
| 2,057,353 A | 10/1936 | Whittlemore, Jr. |
| 2,104,266 A | 1/1938 | McCormick |
| 2,406,275 A | 8/1946 | Wejnarth |
| 2,442,004 A | 5/1948 | Hayward-Butt |
| 2,907,686 A | 10/1959 | Siegel |
| 2,971,039 A | 2/1961 | Western |
| 2,974,669 A | 3/1961 | Ellis |
| 3,062,218 A | 11/1962 | Temkovits |
| 3,200,819 A | 8/1965 | Gilbert |
| 3,255,760 A | 6/1966 | Selker |
| 3,258,015 A | 6/1966 | Ellis et al. |
| 3,280,819 A | 10/1966 | Hazle |
| 3,282,266 A | 11/1966 | Walker, Jr. |
| 3,356,094 A | 12/1967 | Ellis et al. |
| 3,363,633 A | 1/1968 | Weber |
| 3,402,723 A | 9/1968 | Hu |
| 3,482,580 A | 12/1969 | Hollabaugh |
| 3,521,643 A | 7/1970 | Toth |
| 3,559,300 A | 2/1971 | Fox |
| 3,608,560 A | 9/1971 | Briskin et al. |
| 3,681,018 A | 8/1972 | Karl-Georg et al. |
| 3,721,240 A | 3/1973 | Tamburri |
| 3,738,374 A | 6/1973 | Bennett |
| 3,744,496 A | 7/1973 | McCarty et al. |
| 3,804,100 A | 4/1974 | Fariello |
| 3,875,476 A | 4/1975 | Crandall et al. |
| 3,878,041 A | 4/1975 | Leitnaker et al. |
| 3,889,690 A | 6/1975 | Guarnieri |
| 3,895,219 A | 7/1975 | Richerson et al. |
| 3,943,941 A | 3/1976 | Boyd et al. |
| 4,016,061 A | 4/1977 | Wasa et al. |
| 4,068,672 A | 1/1978 | Guerra |
| 4,077,784 A | 3/1978 | Vayrynen |
| 4,083,372 A | 4/1978 | Boden |
| 4,098,725 A | 7/1978 | Yamamoto et al. |
| 4,110,260 A | 8/1978 | Yamamoto et al. |
| 4,131,119 A | 12/1978 | Blasutti |
| 4,141,369 A | 2/1979 | Burruss |
| 4,164,230 A | 8/1979 | Pearlman |
| 4,193,411 A | 3/1980 | Faris et al. |
| 4,215,708 A | 8/1980 | Bron |
| 4,219,032 A | 8/1980 | Tabatznik et al. |
| 4,246,913 A | 1/1981 | Ogden et al. |
| 4,256,945 A | 3/1981 | Carter et al. |
| 4,259,970 A | 4/1981 | Green, Jr. |
| 4,303,083 A | 12/1981 | Burruss, Jr. |
| 4,319,591 A | 3/1982 | Keith et al. |
| 4,327,186 A | 4/1982 | Murata et al. |
| 4,340,072 A | 7/1982 | Bolt |
| 4,393,884 A | 7/1983 | Jacobs |
| 4,407,971 A | 10/1983 | Komatsu et al. |
| 4,416,840 A | 11/1983 | Lee et al. |
| 4,419,302 A | 12/1983 | Nishino et al. |
| 4,431,903 A | 2/1984 | Riccio |
| 4,436,100 A | 3/1984 | Green, Jr. |
| 4,449,039 A | 5/1984 | Fukazawa et al. |
| 4,463,247 A | 7/1984 | Lawrence et al. |
| 4,475,029 A | 10/1984 | Yoshida et al. |
| 4,503,319 A | 3/1985 | Moritoki et al. |
| 4,505,282 A | 3/1985 | Cogbill et al. |
| 4,515,763 A | 5/1985 | Boudart et al. |
| 4,528,121 A | 7/1985 | Matsushita et al. |
| 4,549,905 A | 10/1985 | Yamaguchi et al. |
| 4,555,358 A | 11/1985 | Matsushita et al. |
| 4,562,337 A | 12/1985 | Lawrence |
| 4,570,646 A | 2/1986 | Herron |
| 4,580,583 A | 4/1986 | Green, Jr. |
| 4,621,649 A | 11/1986 | Osterrath |
| 4,623,401 A | 11/1986 | Derbyshire et al. |
| 4,624,828 A | 11/1986 | Alexander |
| 4,634,837 A | 1/1987 | Ito et al. |
| 4,637,407 A | 1/1987 | Bonanno et al. |
| 4,659,912 A | 4/1987 | Derbyshire |
| 4,708,151 A | 11/1987 | Shelar |
| 4,714,082 A | 12/1987 | Banerjee et al. |
| 4,735,217 A | 4/1988 | Gerth et al. |
| 4,765,347 A | 8/1988 | Sensabaugh, Jr. et al. |
| 4,771,796 A | 9/1988 | Myer |
| 4,776,353 A | 10/1988 | Lilja et al. |
| 4,780,299 A | 10/1988 | Kumagai et al. |
| 4,784,978 A | 11/1988 | Ogasawara et al. |
| 4,793,365 A | 12/1988 | Sensabaugh, Jr. et al. |
| 4,799,979 A | 1/1989 | Baldi |
| 4,800,183 A | 1/1989 | Quinby |
| 4,837,421 A | 6/1989 | Luthy |
| 4,846,199 A | 7/1989 | Rose |
| 4,848,376 A | 7/1989 | Lilja et al. |
| 4,851,206 A | 7/1989 | Boudart et al. |
| 4,874,924 A | 10/1989 | Yamamoto et al. |
| 4,877,989 A | 10/1989 | Drews et al. |
| 4,922,901 A | 5/1990 | Brooks et al. |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 4,966,171 A | 10/1990 | Serrano et al. |
| 4,981,522 A | 1/1991 | Nichols et al. |
| 4,991,606 A | 2/1991 | Serrano et al. |
| 4,993,436 A | 2/1991 | Bloom, Jr. |
| 5,016,656 A | 5/1991 | McMurtrie |
| 5,040,552 A | 8/1991 | Schleich et al. |
| 5,042,510 A | 8/1991 | Curtiss et al. |
| 5,045,237 A | 9/1991 | Washburn |
| 5,060,671 A | 10/1991 | Counts et al. |
| 5,076,296 A | 12/1991 | Nystrom et al. |
| 5,085,804 A | 2/1992 | Washburn |
| 5,093,894 A | 3/1992 | Deevi et al. |
| 5,095,921 A | 3/1992 | Losee et al. |
| 5,139,594 A | 8/1992 | Rabin |
| 5,144,962 A | 9/1992 | Counts et al. |
| 5,157,242 A | 10/1992 | Hetherington et al. |
| 5,159,940 A | 11/1992 | Hayward et al. |
| 5,179,966 A | 1/1993 | Losee et al. |
| 5,188,130 A | 2/1993 | Hajaligol et al. |
| 5,224,498 A | 7/1993 | Deevi et al. |
| 5,228,460 A | 7/1993 | Sprinkel et al. |
| 5,235,157 A | 8/1993 | Blackburn |
| 5,249,586 A | 10/1993 | Morgan et al. |
| 5,269,327 A | 12/1993 | Counts et al. |
| 5,274,214 A | 12/1993 | Blackburn |
| 5,285,050 A | 2/1994 | Blackburn |
| 5,322,075 A | 6/1994 | Deevi et al. |
| 5,353,813 A | 10/1994 | Deevi et al. |
| 5,369,723 A | 11/1994 | Counts et al. |
| 5,388,574 A | 2/1995 | Ingebrethsen |

(56) References Cited

U.S. PATENT DOCUMENTS

| | | |
|---|---|---|
| 5,388,594 A | 2/1995 | Counts et al. |
| 5,396,911 A | 3/1995 | Casey, III et al. |
| 5,408,574 A | 4/1995 | Deevi et al. |
| 5,498,855 A | 3/1996 | Deevi et al. |
| 5,505,214 A | 4/1996 | Collins et al. |
| 5,514,630 A | 5/1996 | Willkens et al. |
| 5,591,368 A | 1/1997 | Fleischhauer et al. |
| 5,613,504 A | 3/1997 | Collins et al. |
| 5,665,262 A | 9/1997 | Hajaligol et al. |
| 5,865,185 A | 2/1999 | Collins et al. |
| 5,878,752 A | 3/1999 | Adams et al. |
| 5,894,841 A | 4/1999 | Voges |
| 5,935,975 A | 8/1999 | Rose et al. |
| 6,155,268 A | 12/2000 | Takeuchi |
| 6,196,218 B1 | 3/2001 | Voges |
| 6,234,169 B1 | 5/2001 | Bulbrook et al. |
| 6,592,607 B1 | 7/2003 | Palmer et al. |
| 6,598,607 B2 | 7/2003 | Adiga et al. |
| 6,715,487 B2 | 4/2004 | Nichols et al. |
| 6,772,756 B2 | 8/2004 | Shayan |
| 6,810,883 B2 | 11/2004 | Felter et al. |
| 6,854,470 B1 | 2/2005 | Pu |
| 7,131,599 B2 | 11/2006 | Katase |
| 7,167,641 B2 | 1/2007 | Tam et al. |
| 7,458,374 B2 | 12/2008 | Hale et al. |
| D590,988 S | 4/2009 | Hon |
| D590,989 S | 4/2009 | Hon |
| D590,990 S | 4/2009 | Hon |
| D590,991 S | 4/2009 | Hon |
| 7,527,059 B2 | 5/2009 | Iannuzzi |
| 7,614,402 B2 | 11/2009 | Gomes |
| 7,726,320 B2 | 6/2010 | Robinson et al. |
| 7,832,410 B2 | 11/2010 | Hon |
| 7,845,359 B2 | 12/2010 | Montaser |
| 7,913,688 B2 | 3/2011 | Cross et al. |
| 7,920,777 B2 | 4/2011 | Rabin et al. |
| 7,997,280 B2 | 8/2011 | Rosenthal |
| 8,079,371 B2 | 12/2011 | Robinson et al. |
| 8,127,772 B2 | 3/2012 | Montaser |
| 8,156,944 B2 | 4/2012 | Han |
| 8,365,742 B2 | 2/2013 | Hon |
| 8,371,310 B2 | 2/2013 | Brenneise |
| 8,375,957 B2 | 2/2013 | Hon |
| 8,550,069 B2 | 10/2013 | Alelov |
| 9,420,829 B2 | 8/2016 | Thorens et al. |
| 2002/0146243 A1 | 10/2002 | Rymer |
| 2003/0136404 A1 | 7/2003 | Hindle et al. |
| 2004/0020500 A1 | 2/2004 | Wrenn et al. |
| 2004/0099266 A1 | 5/2004 | Cross et al. |
| 2004/0223917 A1 | 11/2004 | Hindle et al. |
| 2005/0016550 A1 | 1/2005 | Katase |
| 2005/0268911 A1 | 12/2005 | Cross et al. |
| 2006/0191546 A1 | 8/2006 | Takano et al. |
| 2006/0196518 A1 | 9/2006 | Hon |
| 2007/0102013 A1 | 5/2007 | Adams et al. |
| 2007/0267031 A1 | 11/2007 | Hon |
| 2007/0267032 A1 | 11/2007 | Shan |
| 2007/0280653 A1 | 12/2007 | Viera |
| 2008/0017204 A1 | 1/2008 | Braunshteyn et al. |
| 2008/0047571 A1 | 2/2008 | Braunshteyn et al. |
| 2008/0092912 A1 | 4/2008 | Robinson et al. |
| 2008/0230052 A1 | 9/2008 | Montaser |
| 2008/0276947 A1 | 11/2008 | Martzel |
| 2009/0095311 A1 | 4/2009 | Han |
| 2009/0126745 A1 | 5/2009 | Hon |
| 2009/0151717 A1 | 6/2009 | Bowen et al. |
| 2009/0162294 A1 | 6/2009 | Werner |
| 2009/0188490 A1 | 7/2009 | Han |
| 2009/0230117 A1 | 9/2009 | Fernando et al. |
| 2009/0272379 A1 | 11/2009 | Thorens et al. |
| 2010/0024297 A1 | 2/2010 | Suda et al. |
| 2010/0242974 A1 | 9/2010 | Pan |
| 2010/0307518 A1 | 12/2010 | Wang |
| 2011/0036346 A1 | 2/2011 | Cohen et al. |
| 2011/0094523 A1 | 4/2011 | Thorens et al. |
| 2011/0120482 A1 | 5/2011 | Brenneise |
| 2011/0209717 A1 | 9/2011 | Han |
| 2011/0232654 A1 | 9/2011 | Mass |
| 2012/0090630 A1 | 4/2012 | Hon |
| 2016/0198772 A1 | 7/2016 | Thorens et al. |

FOREIGN PATENT DOCUMENTS

| | | |
|---|---|---|
| CA | 2665564 A1 | 4/2008 |
| CN | 87/104459 A | 2/1988 |
| CN | 1040914 | 4/1990 |
| CN | 1205849 A | 1/1999 |
| CN | 1209731 A | 3/1999 |
| CN | 1312730 A | 9/2001 |
| CN | 1744833 A | 3/2006 |
| CN | 2777995 Y | 5/2006 |
| CN | 1788806 A | 6/2006 |
| CN | 2887086 Y | 4/2007 |
| CN | 200983833 Y | 12/2007 |
| CN | 201051862 Y | 4/2008 |
| CN | 201067079 Y | 6/2008 |
| CN | 201085044 Y | 7/2008 |
| CN | 101277623 | 10/2008 |
| CN | 101322579 A | 12/2008 |
| CN | 101442917 A | 5/2009 |
| CN | 101495004 A | 7/2009 |
| CN | 101518361 | 9/2009 |
| CN | 102655773 B | 5/2016 |
| DE | 3640917 A1 | 8/1988 |
| DE | 3735704 A1 | 5/1989 |
| DE | 19854009 A1 | 5/2000 |
| DE | 69824982 T2 | 10/2004 |
| EP | 0893071 A1 | 7/1908 |
| EP | 0117355 A2 | 9/1984 |
| EP | 0236992 A2 | 9/1987 |
| EP | 0277519 A2 | 8/1988 |
| EP | 0295122 A2 | 12/1988 |
| EP | 0358002 A2 | 3/1990 |
| EP | 0358114 A2 | 3/1990 |
| EP | 0430566 A2 | 6/1991 |
| EP | 0438862 A2 | 7/1991 |
| EP | 0488488 A1 | 6/1992 |
| EP | 0503767 A1 | 9/1992 |
| EP | 0845220 A1 | 6/1998 |
| EP | 000845220 B | 6/1998 |
| EP | 0857431 A1 | 8/1998 |
| EP | 1298808 A2 | 4/2003 |
| EP | 1618803 A1 | 1/2006 |
| EP | 1736065 A1 | 12/2006 |
| EP | 1989946 A1 | 11/2008 |
| EP | 2022349 A1 | 2/2009 |
| EP | 2110033 A1 | 10/2009 |
| EP | 2113178 A1 | 11/2009 |
| EP | 2319334 A1 | 5/2011 |
| EP | 2493341 A1 | 9/2012 |
| EP | 2606756 A1 | 6/2013 |
| GB | 2132539 A | 7/1984 |
| GB | 2148079 A | 5/1985 |
| GB | 2148676 A | 5/1985 |
| JP | 61068061 A | 4/1986 |
| JP | 64-17386 | 1/1989 |
| JP | H07-226770 A | 8/1995 |
| JP | H11-089551 A | 4/1999 |
| JP | 3325028 B2 | 9/2002 |
| JP | 2006507909 A | 3/2006 |
| JP | 3768646 B2 | 4/2006 |
| JP | 2006/320286 A | 11/2006 |
| KR | 10-0289448 B1 | 5/2001 |
| KR | 100636287 B1 | 10/2006 |
| KR | 10-2009-0033311 A | 4/2009 |
| KR | 10-2009-0106467 A | 10/2009 |
| RU | 2195849 C2 | 1/2003 |
| RU | 2297781 C2 | 4/2007 |
| WO | WO-86/02528 A1 | 5/1986 |
| WO | WO-9003224 A1 | 4/1990 |
| WO | WO-95/02970 A1 | 2/1995 |
| WO | WO97/48293 | * 12/1997 ............ A24F 40/46 |
| WO | WO-1997-048293 A1 | 12/1997 |
| WO | WO-9823171 A1 | 6/1998 |

(56) References Cited

FOREIGN PATENT DOCUMENTS

| WO | WO-00/28843 A1 | 5/2000 |
|---|---|---|
| WO | WO-03037412 A2 | 5/2003 |
| WO | WO-03/095688 A2 | 11/2003 |
| WO | WO-2004/043175 A1 | 5/2004 |
| WO | WO-2004/050139 A2 | 6/2004 |
| WO | WO-2004/080216 A1 | 9/2004 |
| WO | WO-2004/095955 A1 | 11/2004 |
| WO | WO-2005/099494 A1 | 10/2005 |
| WO | WO-2005120614 A1 | 12/2005 |
| WO | WO-2007024130 A1 | 3/2007 |
| WO | WO-2007/066374 A1 | 6/2007 |
| WO | WO-2007/078273 A1 | 7/2007 |
| WO | WO-2007/098337 A2 | 8/2007 |
| WO | WO-2007/131449 A1 | 11/2007 |
| WO | WO-2007/131450 A1 | 11/2007 |
| WO | WO-2007/141668 A2 | 12/2007 |
| WO | WO-2008/010095 A2 | 1/2008 |
| WO | WO-2008/055423 A1 | 5/2008 |
| WO | WO-2008/070775 A2 | 6/2008 |
| WO | WO-2008/077271 A1 | 7/2008 |
| WO | WO-2008108889 | 9/2008 |
| WO | WO-2010/045671 A1 | 4/2010 |
| WO | WO-2010091593 A1 | 8/2010 |
| WO | WO-2011/050943 A1 | 5/2011 |

OTHER PUBLICATIONS

Eurasian Office Action dated Mar. 5, 2022 for corresponding Eurasian Application No. 202090856, and English-language translation thereof.
European Office Action dated Aug. 2, 2021 for corresponding European Application No. 13157155.6.
Korean Office Action dated Jul. 26, 2021 for corresponding Korean Application No. 10-2020- 7004517, and English-language translation thereof.
Vietnamese Notice of Opposition dated Jul. 15, 2021 for corresponding Application No. 1-2012-01465.
Eurasian Notice of Allowance dated Aug. 28, 2022 for corresponding Eurasian Application No. 202090856, and English-language translation thereof.
Eurasian Office Action dated Oct. 8, 2020 for corresponding Eurasian Application No. 202090856/26, with English-language translation.
Translation of Korean Office Action dated Sep. 9, 2020 for corresponding Korean Application No. 10-2020-7004517.
Modified Substantive Examination issued Nov. 16, 2020 in Malaysian Application No. PI 2012001804.
Re-Issued European Notice of Allowance for corresponding Application No. 17209662.0-1005, dated Sep. 2, 2020.
U.S. Notice of Allowance dated Feb. 2, 2021 for corresponding U.S. Appl. No. 13/220,927.
Brazilian Office Action for corresponding Application No. BR112012010034-3, dated Jul. 15, 2020.
U.S. Office Action issued Sep. 17, 2018 in related U.S. Appl. No. 15/077,226.
Eurasian Patent Office Search dated Dec. 24, 2015 for corresponding Application No. 201500760.
"Excerpt from 'NASA Tech Briefs'," Jul./Aug. 1988, p. 31.
"Joining of Ceramics" by R.E. Loehman et al., published in Ceramic Bulletin, 67(d); 375-380 (1988).
Oxidation Behavior of Silver—and Copper-Based Brazing Filler Metals for Silicon Nitride/Metal Joints by R.R. Kapoor et al., published in J. Am. Ceram. Soc., 72(3):448-454 (1989).
Brazing Ceramic Oxides to Metals at Low Temperatures by J.P Hammond et al., published in Welding Research Supplement, 227-232-s, (1988).
Brazing of Titanium-Vapor-Coated Silicon Nitride by M. L. Santella, published in Advanced Ceramic Materials, 3(5):457-465 (1988).
Microstructure of Alumina Brazed with a Silver-Copper-Titanium Alloy by M.L. Santella et al., published in J. Am. Ceram. Soc., 73(6):1785-1787 (1990).

"High Temperature Structural Silicides" by A.K. Vasudevan et al., Elsevier Science Publishers B.V. (1992).
John A. Dean, Lange's handbook of Chemistry, 12th Edition, 1978 pp. 4-16, 4-123.
Fen et al., "Cyclic oxidation of Haynes 230 alloy", Chapman & Hall, pp. 1514-1520 (1992).
Reinshagen and Sikka, "Thermal Spraying of Selected Aluminides", Proceedings of the Fourth National Thermal Spray Conference, Pittsburgh, PA USA, pp. 307-313 (May 4-10, 1991).
Kutner, "Thermal spray by design", Reprint from Advanced Materials & Processes Incorporating Metal Progress, Oct. (1988).
"Characterizing Thermal Spray Coatings", Article based on presentation made at the Fourth National Thermal Spray Conference, (May 4-10, 1991) and appearing in Advanced Materials and Processes, May 1992, pp. 23-27.
Howes, Jr., "Computerized Plasma Control for Applying Medical-Quality Coatings", Industrial Heating, pp. 22-25, Aug. 1993.
V. Sikka, "Processing of Aluminides", Intermetallic Metallurgy and Processing INtermetallic Compounds, ed stoloff et al., Van Mestrand Reinhold, N.Y., 1994.
K.H. Jack, "The Iron-Nitrogen System: The Crystal Structures of €-Phase Iron Nitrides", Aceta Crystallographica, 5. pp. 404-411 (1952).
K.H. Jack, "Binary and ternary interstitial alloys 1. The iron-nitrogen system: the structures of Fe4N and Fe2N", Proceedings of the Royal Society, A. 195, pp. 34-40 (1948).
K.H. Jack, "The iron-nitrogen system: the preparation and the crystal structures of nitrogen-austenite (Y) and nitrogen-martensite (a)", Proceedings of the Royal Society, A. 208, pp. 200-215 (1952).
European Search Report of Application No. 08251579.2-2313 dated Nov. 7, 2008.
International Preliminary Report on Patentability mailed May 10, 2012 for PCT/EP2010/006534.
International Search Report and Written Opinion mailed Apr. 5, 2011 for PCT/EP2010/006534.
European Search Report dated Mar. 11, 2010 for European Application No. 09252490.
Extended European Search Report for corresponding application No. 13157155.6-1656 dated May 28, 2013.
Summons to Attend Oral Proceeds for European Application No. 10781821.3-1656 dated Dec. 14, 2015.
Communication pursuant to Article 94(3) EPC for European Application No. 10781821.3 dated Feb. 15, 2013.
Columbian Office Action for Application No. 12-86117-7 dated Jul. 25, 2013.
Eurasian Office Action for Application No. 201270596/31 dated Jun. 23, 2014.
Australian Exam Report for Application No. 2010311893 dated Oct. 21, 2015.
Canadian Exam Search Report for Application No. 2,778,786 dated Jun. 19, 2017.
Canadian Exam Search Report for Application No. 2,778,786 dated Sep. 26, 2016.
Chinese First Office Action for Application No. 201080056453.6 dated Jan. 10, 2014.
Chinese First Office Action for Application No. 201610205852.3 dated Mar. 13, 2018.
Chinese Third Office Action for Application No. 201080056453.6 dated May 20, 2015.
Chinese Second Office Action for Application No. 201080056453.6 dated Sep. 5, 2014.
Johns Hopkins Bloomberg School of Public Health, Patrick N. Breysse, Peter S.J. Lees, Particulate Matter, 39 pages, 2006.
Interlocutory decision in Opposition proceedings for European Application No. 10781821.3 dated Dec. 19, 2016.
Notice Of Opposition for European Application No. 10781821.3 dated Jul. 17, 2013.
Indonesian Exam Report for Application No. WO0201202043 dated Dec. 15, 2014.
Israeli Examination Report for Application No. 219338 dated Apr. 29, 2015.
Japanese Notification of Reasons for Refusal for Application No. 2012-535672 dated Sep. 28, 2015.

(56) References Cited

OTHER PUBLICATIONS

Japanese Notification of Reasons for Refusal for Application No. 2012-535672 dated Oct. 1, 2014.
Japanese Decision to Grant a Patent for Application No. 2012-535672 dated Feb. 10, 2016.
Korean Notice of Allowance for Application No. 10-2012-7013165 dated Aug. 28, 2017.
Korean Office Action for Application No. 10-2012-7013165 dated Feb. 24, 2017.
Korean Office Action for Application No. 10-2017-7034102 dated Jan. 19, 2018.
New Zealand Examination Report for Application No. 599821 dated Jan. 16, 2013.
Mexican Office Action for Application No. MX/a/2012/005034 dated Apr. 13, 2015.
International Search Report and Written Opinion for Application No. PCT/EP2010/006534 dated Apr. 5, 2011.
Philippine Exam Report for Application No. 1/2012/500813 dated Jul. 23, 2013.
Philippine Exam Report for Application No. 1/2012/500813 dated Oct. 1, 2013.
Ukrainian Provisional Conclusion of Substantive Examination for Application No. a201206004 dated Dec. 16, 2013.
Ukrainian Conclusion for Application No. a201206004 dated Mar. 18, 2014.
Singapore Invitation to Respond to Written Opinion for Application No. 201203030-0 dated Jun. 21, 2013.
Singapore Examination Report for Application No. 2012030300 dated Jun. 20, 2014.
Australian Notice Of Acceptance for Application No. 2010311893 dated Oct. 28, 2016.
Statement of Grounds of Appeal for European Patent No. 2493341 dated Apr. 20, 2017.
Further Written Submission for European Patent No. 2493341 dated Aug. 19, 2016.
Further Written Submission for European Application No. 10781821.3 dated Jul. 9, 2015.
Chinese Office Action for corresponding Application No. 201610205852.3 dated Oct. 16, 2018, and English translation thereof.
Notice of Opposition for corresponding European Application No. 13157155.6-1005 Nov. 21, 2018.
Eurasian Office Action for corresponding Application No. 201500760/31 dated Nov. 8, 2018, English translation thereof.
Korean Office Action dated Jan. 17, 2019 for corresponding Korean Divisional Patent Application No. 2017-7034102.
United States Office Action for corresponding U.S. Appl. No. 15/077,226 dated Jan. 28, 2019.
United States Office Action for corresponding U.S. Appl. No. 15/220,927 dated Apr. 4, 2019.
"Microstructure of Alumina Brazed with a Silver-Cooper-Titanium Alloy" by M.L. Santella et al., published in J. Am. Ceram. Soc., 73(6):1785-1787 (1990).
K.H. Jack, "The Iron-Nitrogen System: The Crystal Structures of .epsilon.-Phase Iron Nitrides", Aceta Crystallographica, 5. pp. 404-411 (1952).
K.H. Jack, "The iron-nitrogen system: the preparation and the crystal structures of nitrogen-austenite (.gamma.) and nitrogen-martensite (.alpha.)", Proceedings of the Royal Society, A. 208, pp. 200-215 (1952).
European Search Report of Application No. 08251579.2-2313 dated Nov.
Korean Notice of Office Action for corresponding Application No. 10-2019-7010332, dated May 21, 2019, English translation thereof.
Chinese Office Action for corresponding Application No. 201610205852.3, 2019, English translation thereof.
Brazilian Office Action for corresponding Application No. BR112012010034-3, dated Jul. 23, 2019, English translation thereof.
Eurasian Office Action for corresponding Application No. 201500760/31, dated Aug. 21, 2019, English translation thereof.
Korean Notice of Allowance for corresponding Application No. 10-2019-7010332, dated Nov. 19, 2019, English translation thereof.
Chinese Notice of Allowance for Application No. 201610205852.3, dated Mar. 3, 2020.
Eurasian Office Action for corresponding Application No. 201500760, dated Dec. 27, 2019, English translation thereof.
Korean Office Action for corresponding Application No. 10-2020-7004217, dated Mar. 20, 2020, English translation thereof.
European Notice of Allowance for corresponding Application No. 17209662.0, dated Mar. 23, 2020.
Eurasian Notification of Readiness to Grant for Application No. 201500760, dated May 29, 2020.
Korean Office Action dated Aug. 24, 2022 for corresponding Korean Application No. 10-2021-7026848, and English-language translation thereof.
Notice of Allowance dated May 8, 2023 issued in related European patent application No. 21150707.4.
Office Action dated Mar. 29, 2023 issued in related Vietnamese patent application No. 1-2012-01465.
European Notice of Opposition dated Dec. 1, 2021 for corresponding European Application No. 17209662.0.
Korean Office Action dated Oct. 5, 2021 for corresponding Korean Application No. 10-2021-7026848, and English-language translation thereof.
Korean Office Action for corresponding Application No. 10-2020-7004517, dated Jul. 13, 2020.
Extended European Search Report dated May 17, 2021 for corresponding European Application No. 21150707.4.
Notice of Allowance dated Sep. 27, 2023 issued in related European patent application No. 21150707.4.
Office Action dated Jul. 27, 2023 issued in related Korean patent application No. 10-2022-7040837.
Vietnamese Notice of Allowance dated Sep. 28, 2023, issued in corresponding Vietnamese Patent Application No. 1-2012-01465.
European Communication Pursuant to Rule 82(2) dated Jul. 31, 2023 for corresponding European Patent No. 2493341.
Korean Notice of Allowance for corresponding Korean Patent Application No. 2022-7040837 issued on Mar. 14, 2024 and English translation thereof.
Extended European Search Report for Euopean Patent Application No. 24153396.7 mailed on May 21, 2024.

* cited by examiner

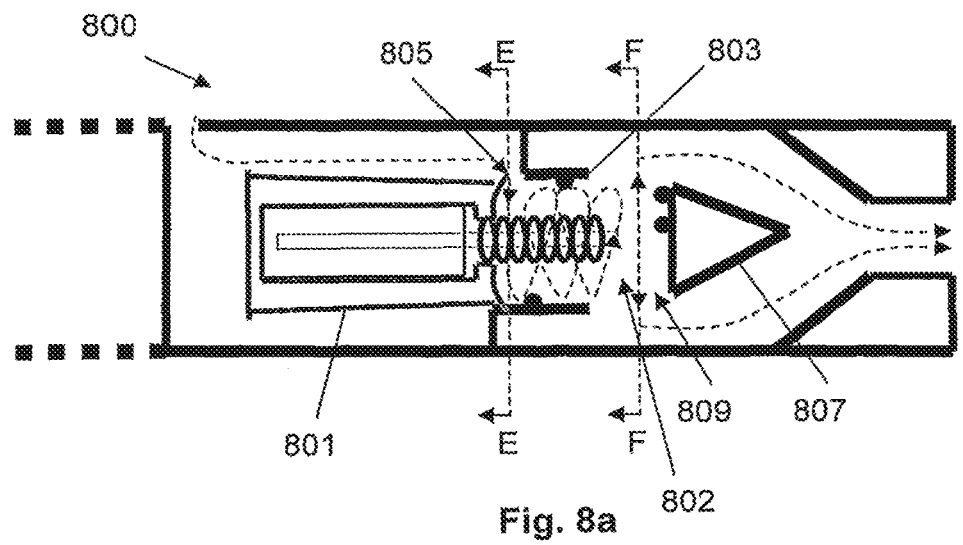
Fig. 8a
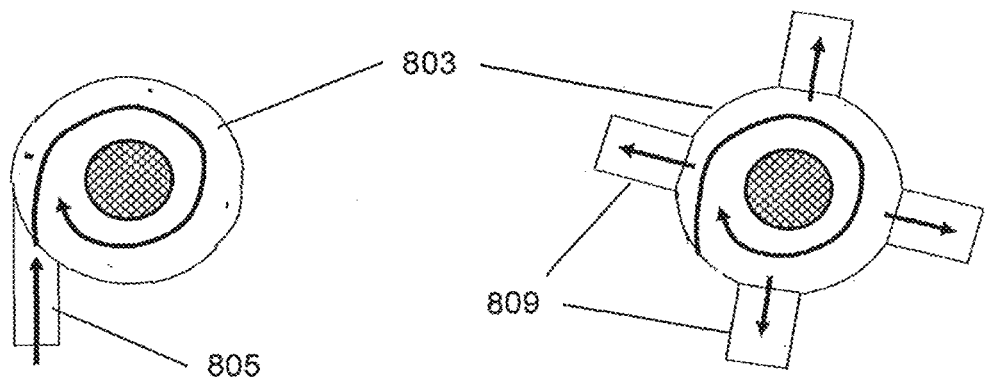
Fig. 8b
Fig. 8c

SMOKING SYSTEM HAVING A LIQUID STORAGE PORTION

CROSS-REFERENCE TO RELATED APPLICATIONS

This is a continuation of U.S. application Ser. No. 15/220,927, filed Jul. 27, 2016, which is a continuation of U.S. application Ser. No. 12/913,510, filed Oct. 27, 2010, which corresponds to and claims priority under 35 U.S.C. § 119 to European Application No. 09252490.9 filed Oct. 27, 2009, the entire content of each of which is hereby incorporated by reference.

BACKGROUND

WO 2007/078273 discloses an electrical smoking system which uses a liquid as an aerosol forming substrate. The liquid is stored in a container formed of a porous material. The container communicates with a heater vaporizer, powered by a battery supply, via a series of small apertures. In use, the heater is activated by the mouth of the user for switching on the battery power supply. Further, suction on the mouthpiece by the user causes air to be drawn through the porous container for liquid, over the heater vaporizer, and into the mouthpiece and subsequently into the mouth of a user.

It is therefore an object of the invention to provide an improved smoking system.

SUMMARY OF SELECTED FEATURES

In a preferred embodiment, a smoking system includes a capillary wick for holding liquid, at least one heater for heating the liquid in at least a portion of the capillary wick to form an aerosol, at least one air inlet, at least one air outlet and a chamber between the air inlet and air outlet, the air inlet, the air outlet and the chamber being arranged so as to define an air flow route from the air inlet to the air outlet via the capillary wick so as to convey the aerosol to the air outlet, and at least one guide for channeling the air flow in the air flow route, so as to control particle size in the aerosol. Preferably, the at least one guide is arranged so that the air flow speed over the wick is greater than the air flow speed upstream of the wick. Also preferably, the at least one guide is arranged to control the particle size of the aerosol to have a diameter substantially less than about 1.5 micrometers.

In the preferred embodiment, the smoking system also includes a housing. In one embodiment, the at least one guide for channelling the air flow is provided by the internal shape of the housing. In another embodiment, the internal shape of the housing at least partially defines the shape of the chamber. In yet another embodiment, the housing is internally shaped downstream of the capillary wick to form an impactor for trapping larger aerosol particles. In still another embodiment, the at least one guide for channelling the air flow is provided by one or more removable inserts contained in the housing. Preferably, at least one of the removable inserts is downstream of the capillary wick and includes an impactor for trapping larger aerosol particles.

In the preferred embodiment, the capillary wick is elongate. In one embodiment, the guides are configured to channel the air flow upstream of the capillary wick in a direction substantially parallel to the longitudinal axis of the capillary wick. In another embodiment, the guides are configured to channel the air flow downstream of the capillary wick in a direction substantially parallel to the longitudinal axis of the capillary wick. In yet another embodiment, the guides are configured to channel the air flow around the capillary wick in a spiral. In still another embodiment, the guides are configured to channel the air flow onto the capillary wick in a direction substantially perpendicular to the longitudinal axis of the capillary wick. In another embodiment, the guides are configured to channel the air flow off the capillary wick in a direction substantially perpendicular to the longitudinal axis of the capillary wick. In still another embodiment, the guides are configured to channel the air flow off the capillary wick in a direction substantially parallel to the longitudinal axis of the capillary wick.

Also in the preferred embodiment, the at least one heater includes a coil of wire at least partially surrounding the capillary wick.

In another embodiment, a smoking system includes a capillary wick for holding liquid, at least one air inlet, at least one air outlet and a chamber between the air inlet and air outlet, the air inlet, the air outlet and the chamber being arranged so as to define an air flow route from the air inlet to the air outlet via the capillary wick so as to convey aerosol formed from the liquid to the air outlet, and at least one guide for channeling the air flow in the air flow route, so as to control particle size in the aerosol.

In still another embodiment, an aerosol delivery system includes a capillary wick for holding liquid, at least one heater for heating the liquid in at least a portion of the capillary wick to form an aerosol, at least one air inlet, at least one air outlet and a chamber between the air inlet and air outlet; the air inlet, the air outlet and the chamber being arranged so as to define an air flow route from the air inlet to the air outlet via the capillary wick so as to convey the aerosol to the air outlet, and at least one guide for channeling air flow in the air flow route, so as to control particle size in the aerosol.

BRIEF DESCRIPTION OF THE DRAWINGS

The invention will be further described, by way of example only, with reference to the accompanying drawings, in which:

FIGS. 8a, 8b and 8c show a seventh embodiment of the smoking system;

DETAILED DESCRIPTION

Figure 1:
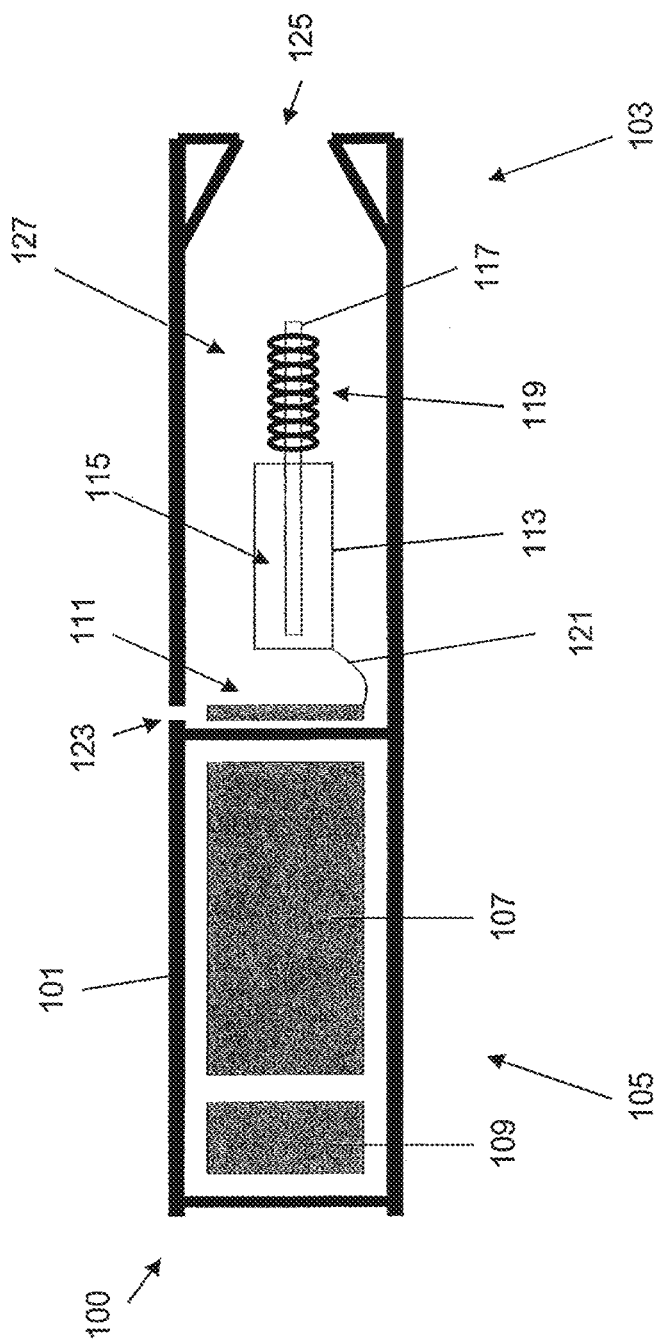
FIG. 1 shows one example of a smoking system having a liquid storage portion.

The present invention relates to a smoking system having a liquid storage portion. In a preferred embodiment, a smoking system includes a capillary wick for holding liquid, at least one heater for heating the liquid in at least a portion of the capillary wick to form an aerosol, at least one air inlet, at least one air outlet and a chamber between the air inlet and air outlet, the air inlet, the air outlet and the chamber being arranged so as to define an air flow route from the air inlet to the air outlet via the capillary wick so as to convey the aerosol to the air outlet, and at least one guide for channeling the air flow in the air flow route, so as to control particle size in the aerosol.

In use, when the heater is activated, the liquid in the at least one portion of the capillary wick is vaporized by the heater to form a supersaturated vapor. The supersaturated vapor is mixed with and carried in the air flow from the at least one air inlet. During the flow, the vapor condenses to form an aerosol in the chamber, and the aerosol is carried towards the air outlet into the mouth of a user. As used herein, the upstream and downstream relative positions are described in relation to the direction of air flow as it is drawn from the air inlet to the air outlet.

The smoking system provides a number of advantages. Most significantly, the at least one guide improves the air and aerosol flow through the smoking system. In particular, the management of the air and aerosol flow through the smoking system by the guides allows either control of the air flow upstream of the capillary wick or control of the air and aerosol flow downstream of the capillary wick or both. Management of the air flow, in particular the air flow direction and the air flow speed, allows the particle size in the resulting aerosol to be controlled and preferably reduced compared with known devices. This improves the smoking experience. In addition, control of the air and aerosol flow can result in higher system efficiency and resulting energy savings.

The liquid has physical properties, for example a boiling point suitable for use in the smoking system: if the boiling point is too high, the at least one heater will not be able to vaporize liquid in the capillary wick, but, if the boiling point is too low, the liquid may vaporize even without the at least one heater being activated. The liquid preferably includes a tobacco-containing material including volatile tobacco flavor compounds which are released from the liquid upon heating. Alternatively, or in addition, the liquid may include a non-tobacco material. For example, the liquid may include water, solvents, ethanol, plant extracts and natural or artificial flavors. Preferably, the liquid further includes an aerosol former. Examples of suitable aerosol formers are glycerine and propylene glycol.

In the preferred embodiment, the smoking system further includes a liquid storage portion. Preferably, the capillary wick is arranged to be in contact with liquid in the liquid storage portion. In that case, in use, liquid is transferred from the liquid storage portion towards the heater by capillary action in the capillary wick. In one embodiment, the capillary wick has a first end and a second end, the first end extending into the liquid storage portion for contact with liquid therein and the at least one heater being arranged to heat liquid in the second end. When the heater is activated, the liquid at the second end of the capillary wick is vaporized by the heater to form the supersaturated vapor.

An advantage of this embodiment is that the liquid in the liquid storage portion is protected from oxygen (because oxygen cannot generally enter the liquid storage portion via the capillary wick) and, in some embodiments light, so that the risk of degradation of the liquid is significantly reduced. Therefore, a high level of hygiene can be maintained. Using a capillary wick extending between the liquid and the heater, allows the structure of the system to be relatively simple. The liquid has physical properties, including viscosity, which allow the liquid to be transported through the capillary wick by capillary action.

The liquid storage portion is preferably a container. Preferably, the liquid storage portion does not include any porous materials, so that there is only a single capillary mechanism (the capillary wick) in the smoking system. This keeps the structure of the smoking system simple and the entire system low-maintenance. Preferably, the container is opaque, thereby limiting degradation of the liquid by light. The liquid storage portion may not be refillable. Thus, when the liquid in the liquid storage portion has been used up, the smoking system is replaced. Alternatively, the liquid storage portion may be refillable. In that case, the smoking system may be replaced after a certain number of refills of the liquid storage portion. Preferably, the liquid storage portion is arranged to hold liquid for a pre-determined number of puffs.

In the preferred embodiment, the capillary wick may have a fibrous or spongy structure. For example, the capillary wick may include a plurality of fibers or threads. The fibers or threads may be generally aligned in the longitudinal direction of the smoking system. Alternatively, the capillary wick may include sponge-like material formed into a rod shape. The rod shape may extend along the longitudinal direction of the smoking system. In the preferred embodiment, the structure of the wick forms a plurality of small bores or tubes, through which the liquid can be transported to the heater, by capillary action.

Preferably, the capillary wick may include any suitable material or combination of materials. Examples of suitable materials are ceramic- or graphite-based materials in the form of fibers or sintered powders. Moreover, the capillary wick may have any suitable capillarity and porosity so as to be used with different liquid physical properties such as density, viscosity, surface tension and vapor pressure. The capillary properties of the wick, combined with the properties of the liquid, ensure that the wick is always wet in the heating area. If the wick is dry, there may be overheating, which can lead to thermal degradation of liquid.

Preferably, the at least one guide channels the air flow by controlling the air flow velocity, that is to say, the speed of the air flow and the direction of the air flow. This may be by directing the air flow in a particular direction. Alternatively or additionally, this may be by controlling the speed of the air flow. The air flow speed may be controlled by varying the cross sectional area of the air flow route, so as to take advantage of the Venturi effect. Air flow through a constricted section increases in speed in order to satisfy the equation of continuity. Similarly, air flow through a wider section decreases in speed.

Preferably, the at least one guide is arranged so that the air flow speed over the wick is greater than the air flow speed upstream of the wick. This is preferably achieved by the guides defining a constricted air flow cross section over the wick, which will force the air flow to accelerate.

Preferably, the at least one guide is arranged to control the particle size of the aerosol to have a diameter substantially less than about 1.5 micrometers ($\mu$m). Even more preferably, the at least one guide is arranged to control the particle size of the aerosol to have a diameter substantially less than about 1.0 micrometers ($\mu$m).

In the preferred embodiment, the smoking system can further include a housing and the at least one guide for channelling the air flow is provided by the internal shape of the housing. That is to say, the internal shape of the assembly itself channels the air flow. Preferably, the inside surface of the housing walls have a shape which forms guides to channel the air flow. The guides provided by the internal shape of the housing may be provided upstream of the capillary wick. In that case, the guides channel the air flow from the air inlet towards the capillary wick. Alternatively or additionally, the guides provided by the internal shape of the housing may be provided downstream of the capillary wick. In that case, the guides channel the aerosol and air flow from the capillary wick towards the air outlet. In the preferred embodiment, the internal shape of the housing defines a tapered channel towards the air outlet.

In another embodiment, the internal shape of the housing may define a linear flow upstream or downstream of the capillary wick. Alternatively, the internal shape of the housing may define a swirled, that is to say, rotating or spiralling, flow upstream or downstream of the capillary wick. In yet another embodiment, the internal shape of the housing may define any turbulent flow upstream or downstream of the capillary wick.

In the preferred embodiment, the smoking system may also include a housing and the internal shape of the housing may at least partially define the shape of the chamber. The size and shape of the chamber affects the air and aerosol flow from the capillary wick towards the air outlet, which affects the process of aerosol formation. This affects the size of the particles in the aerosol. For example, if the chamber is small, this will encourage a fast movement of the aerosol particles towards the air outlet. On the other hand, if the chamber is larger, this may allow more time for the aerosol to form and flow towards the air outlet. The chamber may surround the capillary wick or may be downstream of the capillary wick. The position of the chamber relative to the capillary wick also affects the size of the particles in the aerosol. This is because this affects how quickly the vapor condenses to form the aerosol.

In another embodiment, the smoking system includes a housing and the housing is internally shaped downstream of the capillary wick to form an impactor for trapping larger aerosol particles. Larger aerosol particles may be those aerosol particles which have a diameter greater than about 1.5 micro meters. Alternatively, larger aerosol particles may be those aerosol particles which have a diameter greater than about 1.0 micro meters. Alternatively, larger aerosol particles may include those aerosol particles having another size. The greater inertia of the larger aerosol particles means that, if the air flow route includes a sudden change in direction, the larger aerosol particles may not be able to change direction sufficiently quickly to remain in the air flow route and may, instead, be trapped by the impactor. The impactor is preferably positioned to take advantage of the greater momentum of the larger aerosol particles.

Preferably, the position of the impactor, for example relative to the capillary wick and heater and relative to the chamber, will affect the size and number of particles which are trapped. If the smoking system includes an impactor, the at least one guide may include an acceleration nozzle for directing the aerosol towards the impactor. The nozzle may define a decreasing cross sectional area of the air flow route, so as to accelerate the aerosol towards the impactor. Larger aerosol particles become trapped on the impactor, whereas the smaller aerosol particles can divert around the impactor in the flow route.

In another embodiment, the smoking system further includes a housing, and the at least one guide for channelling the air flow is provided by one or more removable inserts contained in the housing. The one or more removable inserts may include a removable insert upstream of the capillary wick. In that case, the guides channel the air flow from the air inlet towards the capillary wick and heater. Alternatively or additionally, the one or more removable inserts may include a removable insert downstream of the capillary wick. In that case, the guides channel the aerosol and air flow from the capillary wick and heater towards the air outlet. The one or more removable inserts may channel the air flow directly on to the capillary wick and heater. The one or more removable inserts may channel the air flow directly off the capillary wick and heater.

Preferably, the one or more removable inserts may define a linear flow upstream or downstream of the capillary wick and heater. The one or more removable inserts may define a swirled, that is to say, rotating or spiralling, flow upstream or downstream of the capillary wick. The one or more removable inserts may define any turbulent flow upstream or downstream of the capillary wick.

The one or more removable inserts may at least partially define the shape of the chamber. Usually, this will be in combination with the internal shape of the housing, but that is not necessarily the case. The size and shape of the chamber affects the air and aerosol flow from the capillary wick and heater towards the air outlet. This affects the size of the particles in the aerosol. The chamber may surround the capillary wick and heater or may be downstream of the capillary wick and heater. The position of the chamber relative to the capillary wick and heater also affects the size of the particles in the aerosol.

In one embodiment, the one or more removable inserts includes a removable insert surrounding the capillary wick and heater. In that case, preferably the removable insert defines the flow route directly on to the capillary wick and heater and directly off the capillary wick and heater. In one embodiment, the capillary wick is elongate and the removable insert directs the air flow on to the capillary wick in a direction substantially perpendicular to the longitudinal axis of the capillary wick and directs the air flow off the capillary wick in a direction substantially parallel to the longitudinal axis of the capillary wick. Preferably, the smoking system includes an elongate housing and the longitudinal axis of the capillary wick and the longitudinal axis of the housing are substantially parallel. In another embodiment, the capillary wick is elongate and the removable insert directs the air flow on to the capillary wick in a direction substantially perpendicular to the longitudinal axis of the capillary wick and directs the air flow off the capillary wick in a direction substantially perpendicular to the longitudinal axis of the capillary wick. In that case, the air flow on to the capillary wick may be substantially perpendicular to the air flow off the capillary wick. Alternatively, the air flow on to the capillary wick may be substantially in the same direction as the air flow off the capillary wick. Again, preferably, the smoking system includes an elongate housing and the longitudinal axis of the capillary wick and the longitudinal axis of the housing are substantially parallel.

Preferably, at least one of the removable inserts includes bores for channelling the air flow therethrough. The bores may be formed in the insert by machining or, alternatively, by injection molding.

In one embodiment, at least one of the removable inserts is downstream of the capillary wick and includes an impactor for trapping larger aerosol particles. Larger aerosol particles may be those aerosol particles which have a diameter greater than about 1.5 micrometers. Alternatively, larger aerosol particles may be those aerosol particles which have a diameter greater than about 1.0 micrometers. Alternatively, larger aerosol particles may include those aerosol particles having another size. The greater inertia of the larger aerosol particles means that, if the air flow route includes a sudden change in direction, the larger aerosol particles may not be able to change direction sufficiently quickly to remain in the air flow route and may, instead, be trapped by the impactor. The impactor is preferably positioned to take advantage of the greater momentum of the larger aerosol particles.

For example, the removable insert may include a plate positioned downstream of the capillary wick for trapping larger aerosol particles which come into contact with the plate. The plate may be positioned substantially perpendicular to the air flow route. The position of the impactor, for example relative to the capillary wick and heater and relative to the chamber, will affect the size and number of particles which are trapped.

If the smoking system includes an impactor, the at least one guide may include an acceleration nozzle for directing the aerosol towards the impactor. The nozzle may define a decreasing cross sectional area of the air flow route, so as to accelerate the aerosol towards the impactor. Larger aerosol particles become trapped on the impactor, whereas the smaller aerosol particles can divert around the impactor in the flow route.

In the preferred embodiment, the one or more removable inserts may contain any of the liquid storage portion, the capillary wick and the heater. If a removable insert contains the liquid storage portion, the capillary wick and the heater, those parts of the smoking system may be removable from the housing as a single component. This may be useful for refilling or replacing the liquid storage portion, for example.

The guides may be provided by additional components positioned in the flow route. For example, the smoking system may further include pins, grills, perforated tubes, or any other component which may affect the flow route.

In one embodiment, the capillary wick is elongate and the guides are configured to channel the air flow upstream of the capillary wick in a direction substantially parallel to the longitudinal axis of the capillary wick. In that embodiment, the smoking system may be elongate in shape, with the longitudinal axis of the capillary wick being substantially parallel to the longitudinal axis of the smoking system.

In another embodiment, the capillary wick is elongate and the guides are configured to channel the air flow downstream of the capillary wick in a direction substantially parallel to the longitudinal axis of the capillary wick. In that embodiment, the smoking system may be elongate in shape, with the longitudinal axis of the capillary wick being substantially parallel to the longitudinal axis of the smoking system.

In one embodiment, the guides are configured to channel the air flow around the capillary wick in a spiral. In that case, the air may enter the spiral in a tangential direction. The air may exit the spiral in a tangential direction. In that embodiment, the capillary wick may be elongate in shape and the spiral may have an axis which is substantially the longitudinal axis of the capillary wick. The smoking system may be elongate in shape, with the longitudinal axis of the capillary wick being substantially parallel to the longitudinal axis of the smoking system.

In yet another embodiment, the capillary wick is elongate and the guides are configured to channel the air flow onto the capillary wick in a direction substantially perpendicular to the longitudinal axis of the capillary wick. In that embodiment, the smoking system may be elongate in shape, with the longitudinal axis of the capillary wick being substantially parallel to the longitudinal axis of the smoking system.

Alternatively, the guides may be configured to channel the air flow onto the capillary wick in a direction intermediate between the direction of the longitudinal axis of the capillary wick and the direction perpendicular to the longitudinal axis of the capillary wick. That is to say, the guides may channel the air flow onto the capillary wick at a non-90° angle to the capillary wick, that is to say, in a diagonal direction.

In one embodiment, the capillary wick is elongate and the guides are configured to channel the air flow off the capillary wick in a direction substantially perpendicular to the longitudinal axis of the capillary wick. In that embodiment, the smoking system may be elongate in shape, with the longitudinal axis of the capillary wick being substantially parallel to the longitudinal axis of the smoking system.

In another embodiment, the capillary wick is elongate and the guides are configured to channel the air flow off the capillary wick in a direction substantially parallel to the longitudinal axis of the capillary wick. In that embodiment, the smoking system may be elongate in shape, with the longitudinal axis of the capillary wick being substantially parallel to the longitudinal axis of the smoking system.

Alternatively, the guides may be configured to channel the air flow off the capillary wick in a direction intermediate between the direction of the longitudinal axis of the capillary wick and the direction perpendicular to the longitudinal axis of the capillary wick. That is to say, the guides may channel the air flow off the capillary wick at a non-90° angle to the capillary wick, that is to say, in a diagonal direction.

In the preferred embodiment, the at least one heater may include a single heating element. Alternatively, the at least one heater may include more than one heating element, for example two, three, four, five, six or more heating elements. The heating element or heating elements may be arranged appropriately so as to most effectively vaporize liquid in the capillary wick.

The at least one heater preferably includes an electrical heating element. The at least one heater preferably includes an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may include doped or undoped ceramics.

Examples of suitable doped ceramics include doped silicon carbides.

Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver Colorado. In composite materials, the electrically resistive material may optionally be embedded in, encapsulated or coated with an insulating material or vice-versa, depending on the kinetics of energy transfer and the external physicochemical properties required.

The at least one heater may take any suitable form. For example, the at least one heater may take the form of a heating blade. Alternatively, the at least one heater may take the form of a casing or substrate having different electro-conductive portions, or an electrically resistive metallic tube. Alternatively, the at least one heater may be a disk (end) heater or a combination of a disk heater with heating needles or rods. Alternatively, the at least one heater may take the form of a metallic etched foil insulated between two layers of an inert material. In that case, the inert material may include Kapton, all-polyimide or mica foil. Alternatively, the at least one heater may take the form of a sheet of material, which may be rolled around at least a portion of the capillary wick. Alternatively, the at least one heater may take the form of an etched foil folded around at least a portion of the capillary wick. The etched foil may include a metal sheet cut by a laser or by electro-chemical process. The sheet may be made from any suitable material, for example an iron-aluminium based alloy, an iron-manganese-aluminium base alloy or Timetal®. The sheet may be rectangular in shape, or may have a patterned shape which may form a coil-like structure when rolled around the capillary wick. Other alternatives include a heating wire or filament, for example a Ni—Cr, platinum, tungsten or alloy wire.

In one embodiment, the at least one heater includes a coil of wire at least partially surrounding the capillary wick. In that embodiment, preferably the wire is a metal wire. Even more preferably, the wire is a metal alloy wire. The coil may extend fully or partially along the length of the capillary wick. The coil may extend fully or partially around the circumference of the capillary wick. In another embodiment, the coil is not in contact with the capillary wick. This allows the heating coil to heat the capillary wick but reduces wastage by not vaporizing more liquid than necessary. This also reduces the amount of liquid which condenses on the inside walls, thereby reducing cleaning requirements.

Preferably, the at least one heater may heat the liquid in the capillary wick by means of conduction. The heater may be at least partially in contact with the wick. Alternatively, heat from the heater may be conducted to the liquid by means of a heat conductive element. Alternatively, the at least one heater may transfer heat to the incoming ambient air that is drawn through the smoking system during use, which in turn heats the liquid by convection. The ambient air may be heated before passing through the system. Alternatively, the ambient air may be first drawn through the wick and then heated.

In one embodiment, the smoking system is an electrically heated smoking system. In that embodiment, the smoking system may further include an electric power supply. Preferably, the electric power supply includes a cell contained in a housing. The electric power supply may be a Lithium-ion battery or one of its variants, for example a Lithium-ion polymer battery. Alternatively, the power supply may be a Nickel-metal hydride battery, a Nickel cadmium battery, a Lithium-manganese battery, a Lithium-cobalt battery or a fuel cell. In that case, preferably, the electrically heated smoking system is usable by a smoker until the energy in the power cell is used up. Alternatively, the electric power supply may include circuitry chargeable by an external charging portion. In that case, preferably the circuitry, when charged, provides power for a pre-determined number of puffs, after which the circuitry must be re-connected to the external charging portion. An example of suitable circuitry is one or more capacitors or rechargeable batteries.

If the smoking system is an electrically heated smoking system, the smoking system may further include electric circuitry. In one embodiment, the electric circuitry includes a sensor to detect air flow indicative of a user taking a puff. The sensor may be an electro-mechanical device. Alternatively, the sensor may be any of: a mechanical device, an optical device, an opto-mechanical device, a micro electro mechanical systems (MEMS) based sensor and an acoustic sensor. In that case, preferably, the electric circuitry is arranged to provide an electric current pulse to the at least one heater when the sensor senses a user taking a puff. Preferably, the time-period of the electric current pulse is pre-set, depending on the amount of liquid desired to be vaporized. The electric circuitry is preferably programmable for this purpose.

Alternatively, the electric circuitry may include a manually operable switch for a user to initiate a puff. The time-period of the electric current pulse is preferably pre-set depending on the amount of liquid desired to be vaporized. The electric circuitry is preferably programmable for this purpose.

In one embodiment, the at least one air inlet includes two air inlets. Alternatively, there may be three, four, five or more air inlets. Preferably, if there is more than one air inlet, the air inlets are spaced around the housing. In the preferred embodiment, the electric circuitry includes a sensor to detect air flow indicative of a user taking a puff, and the at least one air inlet upstream of the sensor.

Preferably, the smoking system further includes a puff indicator for indicating when the at least one heater is activated. In the embodiment in which the electric circuitry includes a sensor to detect air flow indicative of a user taking a puff, the indicator may be activated when the sensor senses air flow indicative of the user taking a puff. In the embodiment in which the electric circuitry includes a manually operable switch, the indicator may be activated by the switch.

The electrically heated smoking system may further include an atomizer including the at least one heater. In addition to a heating element, the atomizer may include one or more electromechanical elements such as piezoelectric elements. Additionally or alternatively, the atomizer may also include elements that use electrostatic, electromagnetic or pneumatic effects.

Preferably, the smoking system includes a housing. The housing may include a shell and a mouthpiece. In that case, all the components may be contained in either the shell or the mouthpiece. In the case of an electrically heated smoking system, preferably, the electric power supply and the electric circuitry are contained in the shell. Preferably, the liquid storage portion, the capillary wick, the at least one heater and the air outlet are contained in the mouthpiece. The at least one air inlet may be provided in either the shell or the mouthpiece. The guides may be provided in either the shell or the mouthpiece or both the shell and the mouthpiece. Preferably, the mouthpiece is replaceable. Having a shell and a separate mouthpiece provides a number of advantages. First, if the replaceable mouthpiece contains the at least one heater, the liquid storage portion and the wick, all elements which are potentially in contact with the liquid are changed when the mouthpiece is replaced. There will be no cross-contamination in the shell between different mouthpieces, for example ones using different liquids. Also, if the mouthpiece is replaced at suitable intervals, there is little chance of the heater becoming clogged with liquid. Preferably, the shell and mouthpiece are arranged to releasably lock together when engaged.

The housing may include any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably, the smoking system is portable. The smoking system may have a size comparable to a conventional cigar or cigarette.

In one embodiment, a smoking system includes a capillary wick for holding liquid, at least one air inlet, at least one air outlet and a chamber between the air inlet and air outlet, the air inlet, the air outlet and the chamber being arranged so as to define an air flow route from the air inlet to the air outlet via the capillary wick so as to convey aerosol formed from the liquid to the air outlet, and at least one guide for channeling the air flow in the air flow route, so as to control particle size in the aerosol.

In that case, the smoking system may include an atomizer to create the aerosol. The atomizer may include one or more electromechanical elements such as piezoelectric elements. Additionally or alternatively, the atomizer may also include elements that use electrostatic, electromagnetic or pneumatic effects.

Features described in relation to one embodiment of the invention may also be applicable to another embodiment of the invention.

FIG. 1 shows one example of a smoking system 100 having a liquid storage portion. The smoking system 100 of FIG. 1 is an electrically heated smoking system and includes a housing 101 having a mouthpiece end 103 and a body end 105. In the body end 105, there is provided an electric power supply in the form of battery 107 and electric circuitry in the form of circuitry 109 and a puff detection system 111. In the mouthpiece end 103, there is provided a liquid storage portion in the form of cartridge 113 containing liquid 115, a capillary wick 117 and a heating element in the form of heating coil 119. One end of the capillary wick 117 extends into the cartridge 113 and the other end of the capillary wick 117 is surrounded by the heating coil 119. The heating coil 119 is connected to the electric circuitry via connections 121. The housing 101 also includes an air inlet 123, an air outlet 125 at the mouthpiece end 103 and a chamber in the form of aerosol forming chamber 127.

In use, operation is as follows. Liquid 115 is transferred by capillary action from the cartridge 113 from the end of the wick 117 which extends into the cartridge to the other end of the wick 117 which is surrounded by the heating coil 119. When a user draws on the device at the air outlet 125, ambient air is drawn through air inlet 123. In FIG. 1, the puff detection system 111 senses the puff and activates the heating coil 119. The battery 107 supplies a pulse of energy to the heating coil 119 to heat the end of the wick 117 surrounded by the heating coil 119. The liquid in that end of the wick 117 is vaporized by the heating coil 119 to create a supersaturated vapor. At the same time, the liquid being vaporized is replaced by further liquid moving along the wick 117 by capillary action. (This is sometimes referred to as "pumping action".) The supersaturated vapor created is mixed with and carried in the air flow from the air inlet 123. In the aerosol forming chamber 127, the vapor condenses to form an inhalable aerosol, which is carried towards the outlet 125 and into the mouth of the user.

As shown in FIG. 1, the circuitry 109 and the puff detection system 111 are preferably programmable. The circuitry 109 and puff detection system 111 can be used to manage the device operation. This, in conjunction with the physical design of the electrically heated smoking system, can assist with control of the particle size in the aerosol.

The capillary wick can be made from a variety of porous or capillary materials and preferably has a known, pre-defined capillarity. Examples include ceramic- or graphite-based materials in the form of fibers or sintered powders. Wicks of different porosities can be used to accommodate different liquid physical properties such as density, viscosity, surface tension and vapor pressure. The wick must be suitable so that the required amount of liquid can be delivered to the heating coil.

FIG. 1 shows one example of a smoking system which may be used with the present invention. Many other examples are usable with the invention, however. For example, the smoking system need not be electrically operated. For example, additional air inlets may be provided, for example, spaced circumferentially around the housing. For example, a puff detection system need not be provided. Instead, the system could operate by manual operation, for example, the user operating a switch when a puff is taken. For example, the housing could include a separable shell and mouthpiece. For example, the overall shape and size of the housing could be altered. For example, the liquid cartridge may be omitted and the capillary wick could simply be pre-loaded with liquid before use. Other variations are, of course, possible.

A number of embodiments will now be described, based on the example shown in FIG. 1. Components shown in FIG. 1 are not indicated again, in order to simplify the drawings. In addition, the puff detection system 111 and connections 121 are not shown, again for simplicity. Note that FIG. 1 and the following FIGS. 2*a* to 11*l* are schematic in nature. In particular, the components shown are not to scale either individually or relative to one another.

FIGS. 2*a*, 2*b* and 2*c* illustrate a first embodiment of the smoking system. FIG. 2*a* shows a cross sectional view of the mouthpiece end of the first embodiment of the smoking system 200. In FIG. 2*a*, the smoking system 200 includes guides for channelling the air flow within the smoking system. In this embodiment, the guides are provided in removable insert 201 and in the housing inside walls 203. The air flow is shown by the dotted arrows.

Preferably, the removable insert 201 extends across the entire cross section of the smoking system 200 and includes channels 205 for channelling the air flow between the air inlet and the capillary wick and heating coil. In this embodiment, the liquid cartridge, the capillary wick and the heating coil all form part of the removable insert 201, although this need not be the case. The channels 205 taper inward to direct the air flow generally in the direction of the longitudinal axis of the housing but diagonally towards the capillary wick and heating coil.

In addition, the housing inside walls 203 are shaped to form the aerosol forming chamber 202 and provide guides for channelling the air and aerosol flow between the capillary wick and heating coil and the air outlet, through the aerosol forming chamber 202. In this embodiment, the housing inside walls 203 are tapered towards the air outlet, thereby direct the air and aerosol flow substantially in the direction of the longitudinal axis of the housing.

FIGS. 2*b* and 2*c* are cross sections along line A-A of FIG. 2*a*. FIGS. 2*b* and 2*c* show two alternative arrangements for the channels 205 in removable insert 201. Although the cross section of the device is shown as circular in FIGS. 2*a*, 2*b* and 2*c*, this need not be the case. In FIG. 2*b*, the inlet of each channel is circumferentially aligned with the outlet of the channel. In FIG. 2*c*, the channels 205 are twisted around the axis of the housing. That is to say, the inlet of each channel is shifted circumferentially with respect to the outlet of the channel. Preferably, the insert 201 includes a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example.

Figure 2A:
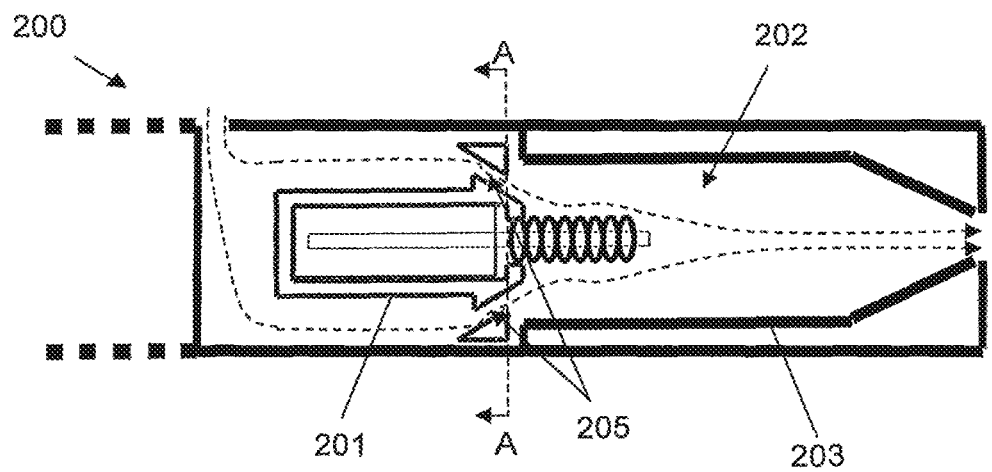
FIGS. 2a, 2b and 2c show a first embodiment of the smoking system.
Figures 2B, 2C:
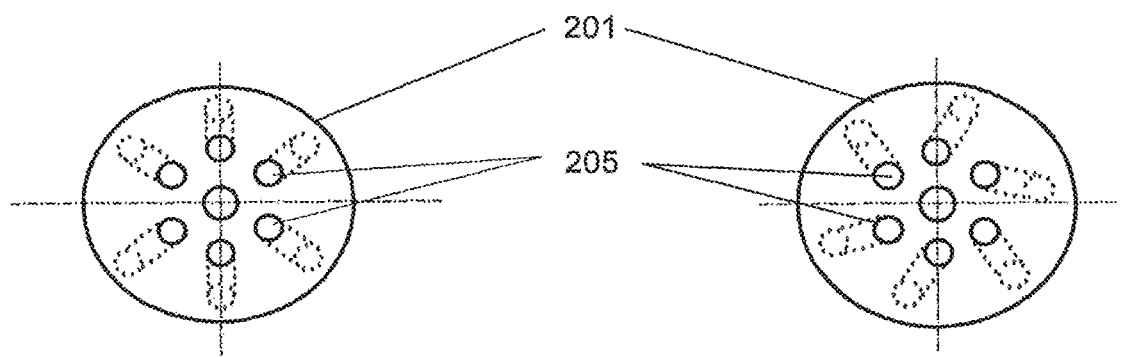

The embodiment shown in FIGS. 2a, 2b and 2c provides a substantially axially directed incoming air flow from the air inlet to the capillary wick and heating coil and a substantially axially directed outgoing air flow from the capillary wick and heating coil to the air outlet. It has been found that managing the air flow in this way improves the aerosol formation occurring within the smoking system. The guides provided by insert 201 channel the air flow so as to concentrate air flow onto the wick and heating element and so as to increase turbulence. This decreases the particle size of the aerosol inhaled by a user. The guides provided by the housing inside walls 203 reduce the volume of the aerosol forming chamber 202 in the smoking system and therefore improve aerosol flow towards the air outlet. This improves the smoking experience. The arrangement of FIG. 2c encourages a swirled airflow to improve aerosol formation even further.

A number of variations are possible in the smoking system of FIGS. 2a, 2b and 2c. First, more than one air inlet may be provided. The guides upstream of the capillary wick and heating coil may be formed as one or more removable portions (insert 201, as shown) or alternatively as an integral part of the housing or as a combination of both. Similarly, the guides downstream of the capillary wick and heating coil may be formed as one or more removable portions or alternatively as an integral part of the housing (shaped housing inside walls 203, as shown) or as a combination of both. Any number of channels 205 may be formed in the insert 201. The channels may be evenly or non-evenly distributed circumferentially around the insert. The channels may be arranged as several rows forming circles of different diameters. The channels may have a constant cross sectional shape and area along their length, or the cross sectional shape can vary along the length. The channels may include some channels having different cross sectional shapes and areas from others. The channels may be formed in the insert by machining. Alternatively, the insert may be formed together with the channels by injection molding. The channels may be formed at any appropriate angle to the longitudinal axis of the housing. The housing inside walls 203 may be shaped appropriately for the desired volume and shape of the aerosol forming chamber 202 within the smoking system.

Figure 3A:
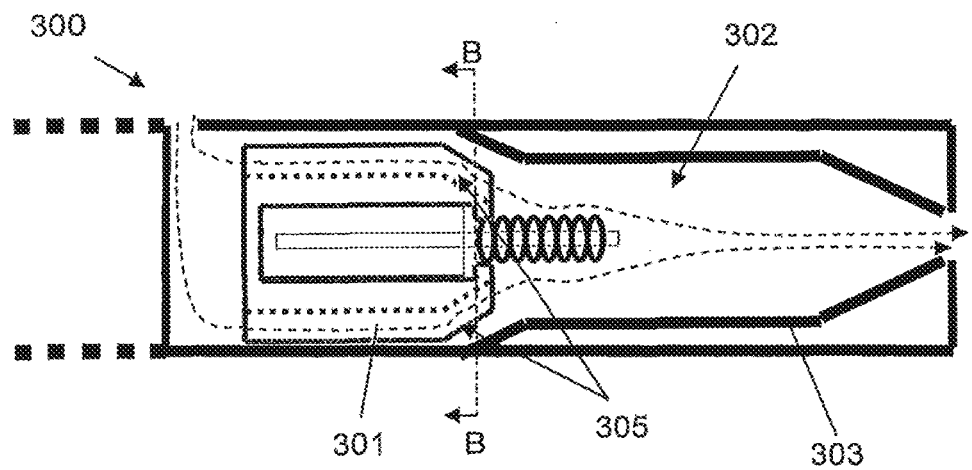
FIGS. 3a and 3b show a second embodiment of the smoking system.
Figure 3B:
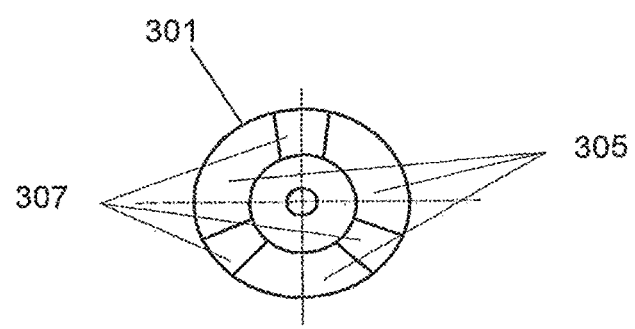

FIGS. 3a and 3b show a second embodiment of the smoking system. FIG. 3a shows a cross sectional view of the mouthpiece end of the second embodiment of the smoking system 300. In FIG. 3a, the smoking system 300 includes guides for channelling the air flow within the smoking system. In this embodiment, the guides are provided in removable insert 301 and in the housing inside walls 303. The air flow is shown by the dotted arrows.

Just like removable insert 201 in FIGS. 2a, 2b and 2c, removable insert 301 of FIGS. 3a and 3b extends across the entire cross section of the smoking system. However, in this embodiment, it also extends further upstream than the insert 201 of FIGS. 2a, 2b and 2c. The removable insert 301 includes channels 305 for channelling the air flow between the air inlet and the capillary wick and heating coil. The channels 305 extend in the direction of the longitudinal axis of the housing at their upstream end, then taper inward at their downstream end. The channels 305 direct the air flow generally in the direction of the longitudinal axis of the housing initially, then diagonally towards the capillary wick and heating coil. In this embodiment, the liquid cartridge, the capillary wick and the heating coil all form part of the removable insert 301, although this need not be the case.

In addition, the housing inside walls 303 are shaped to form the aerosol forming chamber 302 and to provide guides for channelling the air and aerosol flow between the capillary wick and heating coil and the air outlet, through the aerosol forming chamber 302. In this embodiment, the housing inside walls 303 are tapered towards the air outlet and thereby direct the air and aerosol flow substantially in the direction of the longitudinal axis of the housing.

FIG. 3b is a cross section along line B-B of FIG. 3a. Although the cross section of the device is shown as circular in FIG. 3b, this need not be the case. Referring to FIG. 3b, the insert 301 includes channels 305. Around the circumference of the insert 301 are several contact zones 307 for contacting with the inside of the housing. That is to say, the channels are formed by assembly of the insert in the housing. Preferably, the insert 301 includes a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example.

The embodiment shown in FIGS. 3a and 3b provides a substantially axially directed incoming air flow from the air inlet to the capillary wick and heating coil and a substantially axially directed outgoing air flow from the capillary wick and heating coil to the air outlet. It has been found that managing the air flow in this way improves the aerosol formation occurring within the smoking system. The guides provided by insert 301 channel the air flow so as to concentrate air flow onto the wick and heating element and so as to increase turbulence. This decreases the particle size of the aerosol inhaled by a user. The guides provided by the housing inside walls 303 reduce the volume of the aerosol forming chamber 302 in the smoking system and therefore improve aerosol flow towards the air outlet. This improves the smoking experience.

A number of variations are possible in the smoking system of FIGS. 3a and 3b. First, more than one air inlet may be provided. The guides upstream of the capillary wick and heating coil may be formed as one or more removable portions (insert 301, as shown) or alternatively as an integral part of the assembly or as a combination of both. Similarly, the guides downstream of the capillary wick and heating coil may be formed as one or more removable portions or alternatively as an integral part of the assembly (shaped housing inside walls 303, as shown) or as a combination of both. Any number of channels 305 may be formed in the insert 301. The channels may be evenly or non-evenly distributed circumferentially around the insert. The channels may be arranged as several rows forming circles of different diameters. The channels may have a constant cross sectional shape and area along their length, or the cross sectional shape can vary along the length. The channels may include some channels having different cross sectional shapes and areas from others. The channels may be formed in the insert by machining. Alternatively, the insert may be formed together with the channels by injection molding. The channels may be formed at any appropriate angle to the longitudinal axis of the housing. As in FIG. 2c, the channels may be twisted around the axis of the housing, so as to encourage a swirled airflow. The housing inside walls 303 may be shaped appropriately for the desired volume and shape of the aerosol forming chamber 302 within the smoking system.

Figure 4:
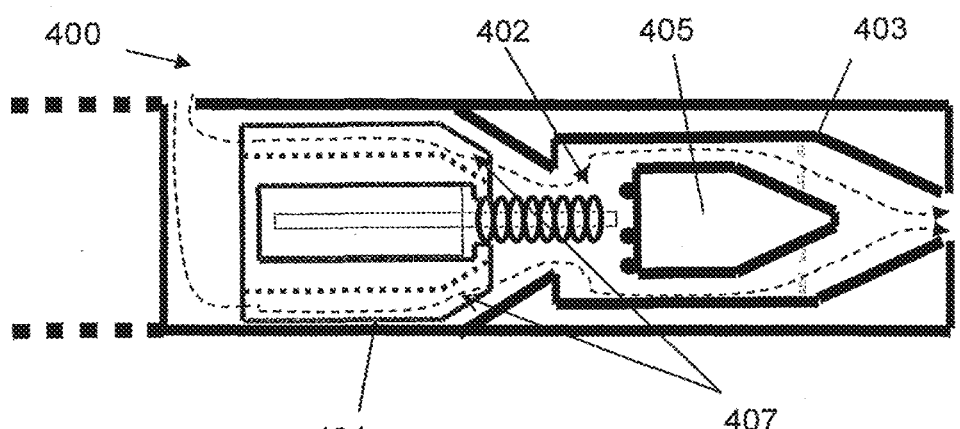
FIG. 4 shows a third embodiment of the smoking system.

FIG. 4 shows a cross sectional view of the mouthpiece end of the third embodiment of the smoking system 400. In FIG. 4, the smoking system 400 includes guides for channelling the air flow within the smoking system. In this embodiment, the guides are provided by removable insert 401, by the housing inside walls 403 and by impactor 405. The air flow is shown by the dotted arrows.

The removable insert 401 is similar to removable insert 301 shown in FIGS. 3a and 3b and extends across the entire cross section of the smoking system 400. The removable insert 401 includes channels 407 for channelling the air flow between the air inlet and the capillary wick and heating coil. The channels 407 extend in the direction of the longitudinal axis of the housing at their upstream end, then taper inward at their downstream end. The channels 407 direct the air flow generally in the direction of the longitudinal axis of the housing initially, then diagonally towards the capillary wick and heating coil. In this embodiment, the liquid cartridge, the capillary wick and the heating coil all form part of the removable insert 401, although this need not be the case. Preferably, the insert 401 includes a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example. The insert could alternatively take the form shown in FIG. 2a or another suitable form.

In addition, the housing inside walls 403 and impactor 405 provide guides for channelling the aerosol flow between the capillary wick and heating coil and the air outlet. The housing inside walls 403 and impactor 405 also form the aerosol forming chamber 402. In this embodiment, the housing inside walls are shaped so as to direct the flow away from the heating coil in the radial direction, that is to say, substantially perpendicular to the longitudinal axis of the housing. Preferably, the impactor 405 includes a removable insert which may be positioned in the center of the device, supported by the housing walls (see dotted lines). The impactor 405 allows larger aerosol particles to be trapped on its upstream side. This produces a filtering effect and reduces the average particle size. This is shown schematically in FIG. 4. Then, the housing inside walls 403 and impactor 405 direct the air flow towards the air outlet.

The embodiment shown in FIG. 4 also provides a substantially axially directed incoming air flow from the air inlet to the capillary wick and heating coil and a substantially radially directed air flow downstream of the capillary wick and heating coil. It has been found that managing air flow in this way improves the aerosol formation occurring within the smoking system. The guides provided by insert 401 channel the air flow so as to concentrate air flow onto the wick and heating element and so as to increase turbulence. This decreases the particle size of the aerosol inhaled by a user. The guides provided by the housing inside walls 403 and impactor allow larger aerosol particles to be trapped and prevented from exiting through the air outlet. The arrangement allows the capillary wick and heating coil to be supplied with cool, non-saturated air, in order to decrease the aerosol particle size. This improves the smoking experience.

A number of variations are possible in the smoking system of FIG. 4. First, although the cross section of the device is shown as circular in FIG. 4, this need not be the case. Second, more than one air inlet may be provided. The guides upstream of the capillary wick and heating coil may be formed as one or more removable portions (insert 401, as shown) or alternatively as an integral part of the housing or as a combination of both. Similarly, the guides downstream of the capillary wick and heating coil may be formed as one or more removable portions or alternatively as an integral part of the housing or as a combination of both (shaped housing inside walls 403 combined with removable impactor 405, as shown). Any number of channels 407 may be formed in the insert 401. The channels may be evenly or non-evenly distributed circumferentially around the insert. The channels may be arranged as several rows forming circles of different diameters. The channels may have a constant cross sectional shape and area along their length, or the cross sectional shape can vary along the length. The channels may include some channels having different cross sectional shapes and areas from others. The channels may be formed in the insert by machining. Alternatively, the insert may be formed with the channels by injection molding. The channels may be formed at any appropriate angle to the longitudinal axis of the housing. As in FIG. 2c, the channels may be twisted around the axis of the housing, so as to encourage a swirled airflow. The housing inside walls 403 and impactor 405 may be shaped and sized appropriately for the desired volume and shape of the aerosol forming chamber 402 within the smoking system. The impactor 405 may be formed with any appropriate shape and is preferably designed in conjunction with the shaped housing inside walls 403, in order to channel the air and aerosol flow as desired.

Figure 5A:
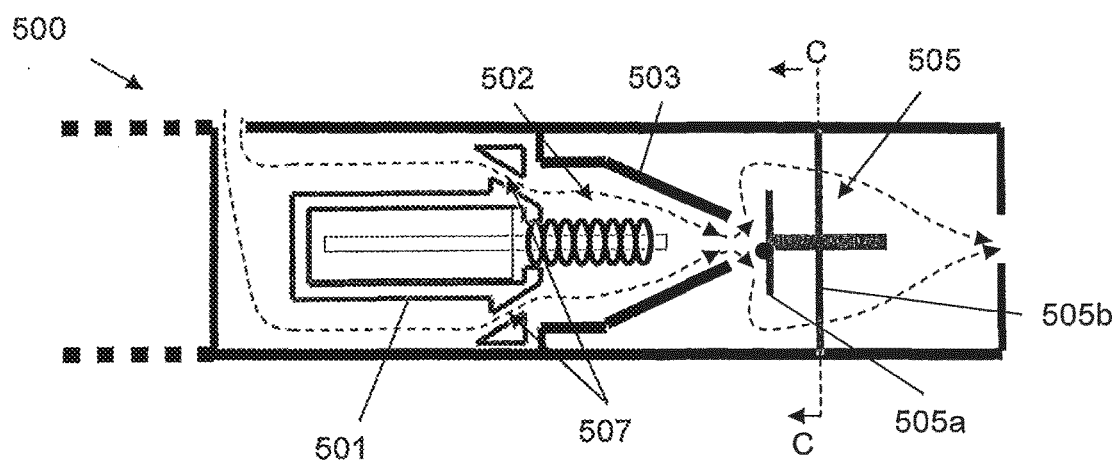
FIGS. 5a and 5b show a fourth embodiment of the smoking system.
Figure 5B:
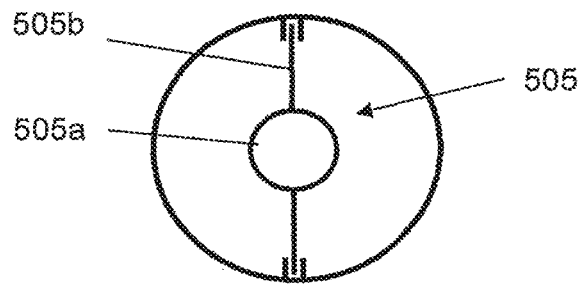

FIGS. 5a and 5b show a fourth embodiment of the smoking system. FIG. 5a shows a cross sectional view of the mouthpiece end of the fourth embodiment of the smoking system 500. In FIG. 5a, the smoking system 500 includes guides for channelling the air flow within the smoking system. In this embodiment, the guides are provided by removable insert 501, by the housing inside walls 503 and by impactor 505.

The removable insert 501 is similar to removable insert 201 shown in FIGS. 2a, 2b and 2c, extends across the entire cross section of the smoking system 500, and includes channels 507 for channelling the air flow between the air inlet and the capillary wick and heating coil. In this embodiment, the liquid cartridge, the capillary wick and heating coil all form part of the removable insert 501, although this need not be the case. The channels 507 taper inward to direct the air flow generally in the direction of the longitudinal axis of the housing but diagonally towards the capillary wick and heating coil. Preferably, the insert 501 includes a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example. The insert could alternatively take the form shown in FIGS. 3a and 4 or another suitable form.

In addition, the housing inside walls 503 are tapered inward to form the aerosol forming chamber 502. The housing inside walls 503 together with the impactor 505 provide guides for channelling the aerosol flow between the capillary wick and heating coil and the air outlet. In this embodiment, the housing inside walls 503 are shaped so as to form a nozzle to direct and accelerate the air flow substantially in the axial direction. Preferably, impactor 505 is located directly downstream of the aerosol forming chamber.

FIG. 5b is a cross section along line C-C of FIG. 5a. The impactor 505 acts to trap larger aerosol particles and therefore provides a filtering effect. The impactor 505 includes a plate 505a which may be positioned in the center of the housing, supported at the housing walls by struts 505b. The plate 505*a* acts to trap the larger aerosol particles exiting the aerosol forming chamber 502.

The embodiment shown in FIGS. 5*a* and 5*b* provides an accelerated, substantially axially directed air flow downstream of the capillary wick and heating coil. It has been found that managing the air flow in this way improves the aerosol formation occurring within the smoking system. The guides provided by insert 501 channel the air flow so as to concentrate air flow onto the wick and heating element and so as to increase turbulence. This decreases the particle size of the aerosol inhaled by a user. The tapered nozzle shape provided by the housing inside walls 503 accelerate the aerosol downstream towards the impactor 505 and the plate 505*a* of the impactor 505 traps larger aerosol particles to prevent them exiting through the air outlet. The arrangement allows the capillary wick and heating coil to be supplied with cool, non-saturated air, in order to decrease the aerosol particle size. It also allows any larger aerosol particles that do form to be filtered out of the flow. This improves the smoking experience.

A number of variations are possible in the smoking system of FIGS. 5*a* and 5*b*. First, although the cross section of the device is shown as circular in FIGS. 5*a* and 5*b*, this need not be the case. Second, more than one air inlet may be provided. The guides upstream of the capillary wick and heating coil may be formed as one or more removable portions (insert 501, as shown) or alternatively as an integral part of the housing or as a combination of both. Similarly, the guides downstream of the capillary wick and heating coil may be formed as one or more removable portions or alternatively as an integral part of the housing or as a combination of both (shaped housing inside walls 503 combined with removable impactor 505, as shown). Any number of channels 507 may be formed in the insert 501. The channels may be evenly or non-evenly distributed circumferentially around the insert. The channels may be arranged as several rows forming circles of different diameters. The channels may have a constant cross sectional shape and area along their length, or the cross sectional shape can vary along the length. The channels may include some channels having different cross sectional shapes and areas from others. The channels 507 may be twisted around the axis of the housing to provide a swirled air flow. The channels may be formed in the insert by machining. Alternatively, the insert may be formed together with the channels by injection molding. The channels may be formed at any appropriate angle to the longitudinal axis of the housing.

The housing inside walls 503 may be shaped appropriately for the desired volume and shape of the aerosol forming chamber 502 within the smoking system and for the desired acceleration of the aerosol towards the impactor 505. The impactor may be formed by machining or injection molding. The shape and size of the impactor plate 505*a* may be varied. The distance between the downstream end of the aerosol forming chamber 502 and the impactor plate may be varied.

FIGS. 6*a* to 6*e* each show a cross sectional view of the mouthpiece end of a fifth embodiment of the smoking system. In each of FIGS. 6*a* to 6*e*, the smoking system includes guides for channelling the air flow within the smoking system. The air flow is shown by the dotted arrows.

Figure 6A:
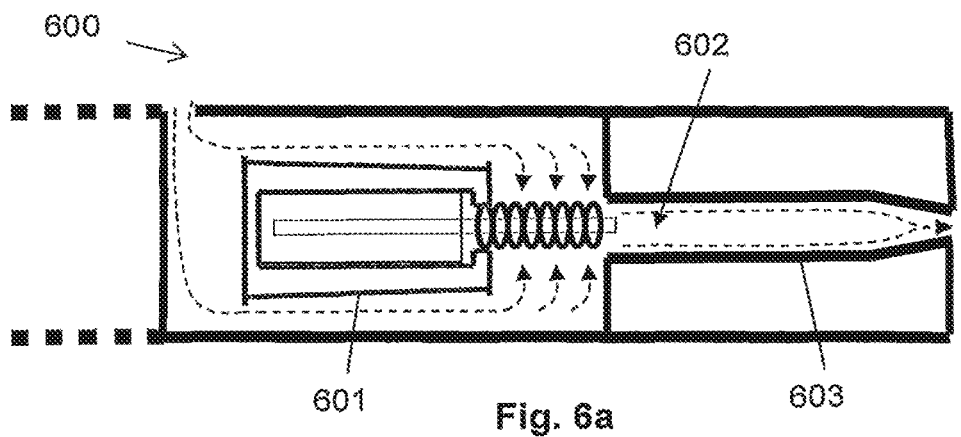
FIGS. 6a, 6b, 6c, 6d and 6e show a fifth embodiment of the smoking system.

FIG. 6*a* shows a first arrangement of the smoking system 600. In FIG. 6*a*, the guides are provided by removable insert 601 and by the housing inside walls 603. The removable insert 601 extends only across the center of the smoking system 600, thereby directing the air flow between the air inlet and the capillary wick and heating coil to the outer circumference of the device. The removable insert 601 is shaped so that, at the capillary wick and heating coil, the air flow is directed onto the capillary wick and heating coil in a substantially radial direction, that is to say, substantially perpendicular to the longitudinal axis of the housing. In FIGS. 6*a* to 6*e*, the liquid cartridge, the capillary wick and the heating coil all form part of the removable insert 601, although this need not be the case.

In addition, the housing inside walls 603 provide guides for channelling the air and aerosol flow between the capillary wick and heating coil and the air outlet. The housing inside walls 603 also define the aerosol forming chamber 602. In this embodiment, the housing inside walls 603 are shaped so as to direct the air and aerosol flow substantially in the direction of the longitudinal axis of the housing.

Figure 6B:
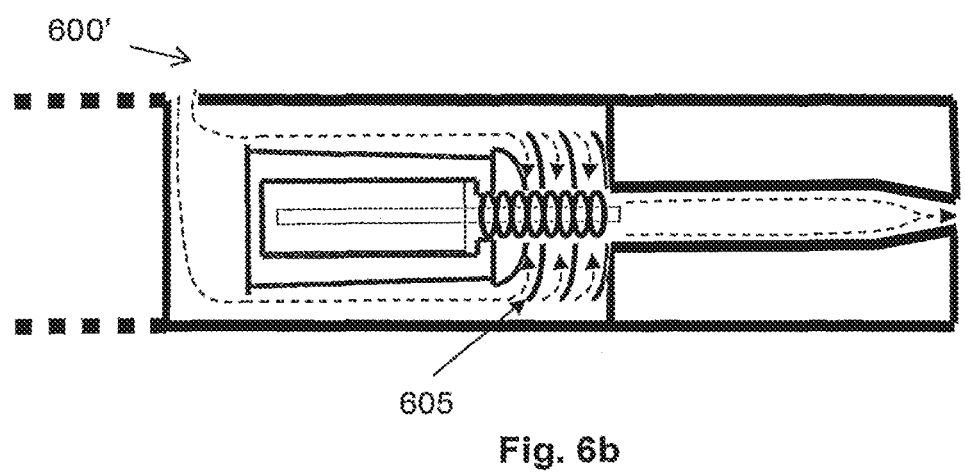

FIG. 6*b* shows a second arrangement of the smoking system 600'. The arrangement shown in FIG. 6*b* is identical to that shown in FIG. 6*a* except that an additional insert 605 is provided in the smoking system 600' of FIG. 6*b*. The additional insert 605 provides additional guides for directing air flow. The insert 605 is a ribbed insert surrounding the capillary wick and heating coil. It is shaped so as to direct the air flow onto the capillary wick and heating coil in a substantially radial direction, that is to say, substantially perpendicular to the longitudinal axis of the housing.

Figure 6C:
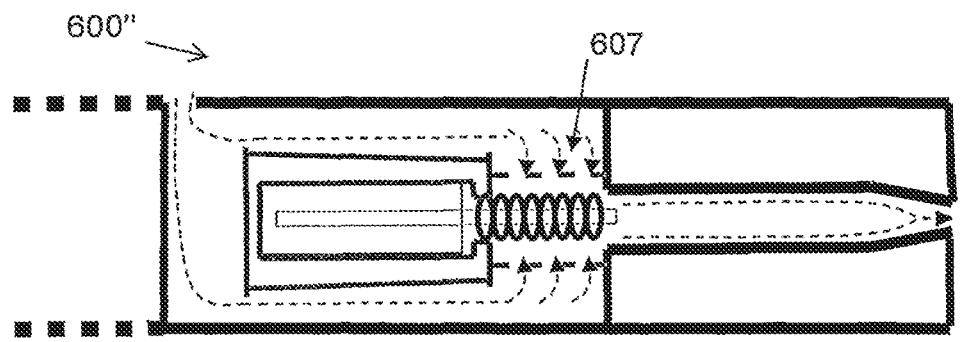

FIG. 6*c* shows a third arrangement of the smoking system 600". The arrangement shown in FIG. 6*c* is identical to that shown in FIG. 6*a* except that an additional insert 607 is provided in the smoking system 600" of FIG. 6*c*. The additional insert 607 provides additional guides for directing air flow. The insert 607 is a grill insert including a tube having a number of longitudinally spaced holes. The insert 607 surrounds the capillary wick and heating coil and directs the air flow through the holes in the grill and onto the capillary wick and heating coil in a substantially radial direction, that is to say, substantially perpendicular to the longitudinal axis of the housing.

Figure 6D:
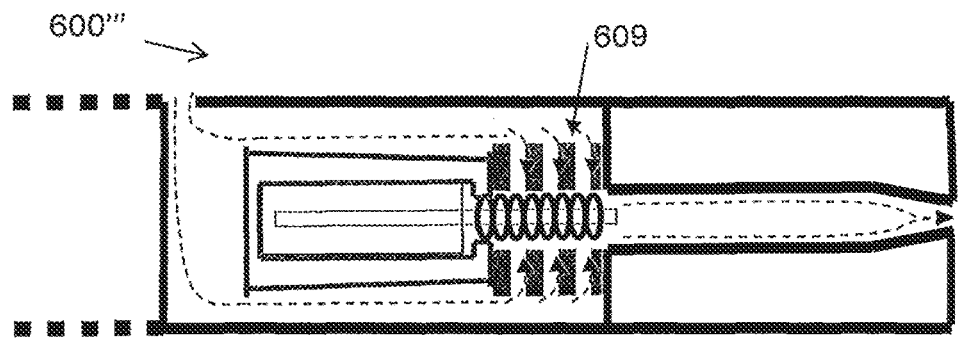

FIG. 6*d* shows a fourth arrangement of the smoking system 600'''. The arrangement shown in FIG. 6*d* is identical to that shown in FIG. 6*a* except that an additional insert 609 is provided in the smoking system 600''' of FIG. 6*d*. The additional insert 609 provides additional guides for directing air flow. The insert 609 is a grooved insert including a solid cylindrical tube having a number of channels formed in the radial direction. The insert 609 surrounds the capillary wick and heating coil and directs the air flow through the radial channels and onto the capillary wick and heating coil in a substantially radial direction, that is to say, substantially perpendicular to the longitudinal axis of the housing.

Figure 6E:
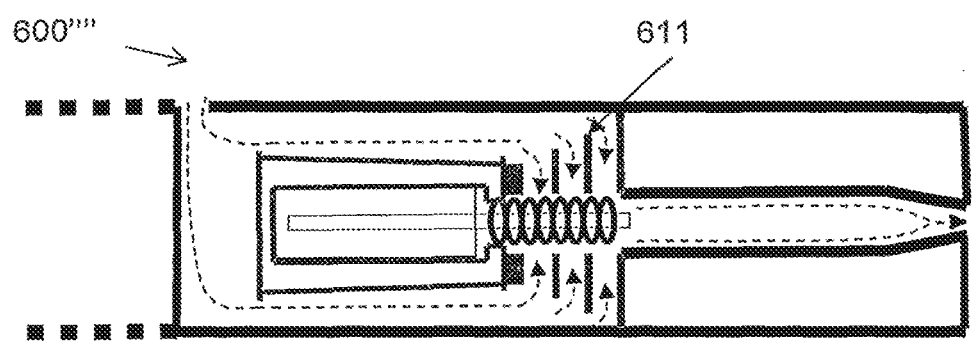

FIG. 6*e* shows a fifth arrangement of the smoking system 600''''. The arrangement shown in FIG. 6*e* is identical to that shown in FIG. 6*a* except that an additional insert 611 is provided in the smoking system 600'''' of FIG. 6*e*. The additional insert 611 provides additional guides for directing air flow. The insert 611 is a grooved insert including a solid conical tube having a number of channels formed in the radial direction. The insert 611 surrounds the capillary wick and heating coil and directs the air flow through the radial channels and onto the capillary wick and heating coil in a substantially radial direction, that is to say, substantially perpendicular to the longitudinal axis of the housing.

The embodiments shown in FIG. 6*a* to 6*e* provide a substantially radially directed air flow onto the capillary wick and heating coil and a substantially axially directed air and aerosol flow downstream of the capillary wick and heating coil. It has been found that managing air flow in this way improves the aerosol formation occurring within the smoking system. The guides provided by the insert 601, and the additional insert 605, 607, 609, 611 if present, channel the air flow as to direct the air flow onto the capillary wick and heating coil in a substantially radial direction. This provides the capillary wick and heating coil with cool, non-saturated air, which decreases the particle size of the aerosol inhaled by a user. The guides provided by the housing inside walls 603 reduce the volume of the cavity in the smoking system and therefore improve aerosol flow towards the air outlet. This improves the smoking experience.

A number of variations are possible in the smoking systems of FIGS. 6*a* to 6*e*. First, although the cross section of the device is shown as circular in FIGS. 6*a* to 6*e*, this need not be the case. Second, more than one air inlet may be provided. The guides upstream of the capillary wick and heating coil may be formed as one or more removable portions (inserts 601, 605, 607, 609 and 611, as shown) or alternatively as an integral part of the housing or as a combination of both. Similarly, the guides downstream of the capillary wick and heating coil may be formed as one or more removable portions or alternatively as an integral part of the housing (shaped housing inside walls 603, as shown) or as a combination of both. The insert 601 is shown without channels, although longitudinal channels towards the outside of the insert may be provided. In addition, if channels are provided, the insert may extend across the entire cross section of the housing. Any configuration of channels may be provided. The channels may be twisted around the axis of the housing, so as to encourage a swirled airflow. The channels in inserts 601, 605, 609, 611 and the holes in insert 607 may be formed by machining. Alternatively, the insert may be formed with channels or holes already formed, by injection molding. Any number of holes or channels may be formed in inserts 605, 607, 609, 611. Preferably, the insert 601 includes a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example. The inserts 605, 607, 609, 611 may also be provided with such a locating pin or protrusion. The housing inside walls 603 may be shaped appropriately for the desired volume and shape of the aerosol forming chamber within the smoking system.

Figure 7A:
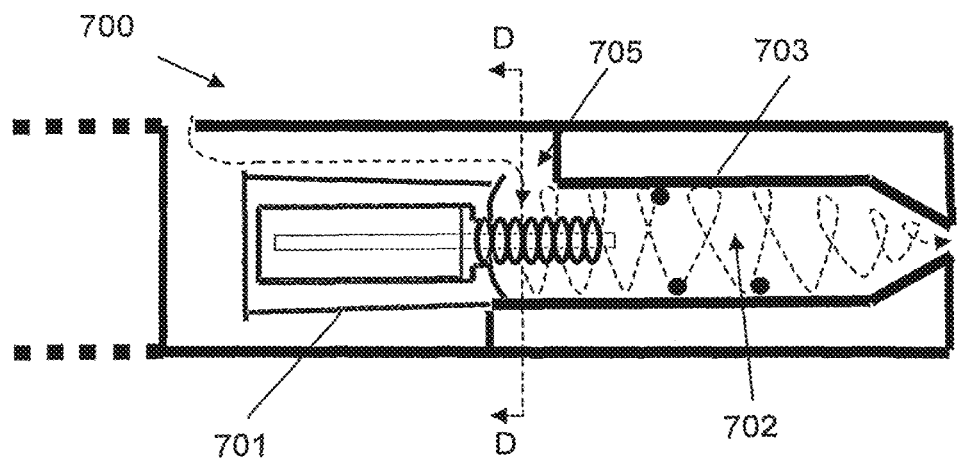
FIGS. 7a, 7b and 7c show a sixth embodiment of the smoking system.
Figures 7B, 7C:
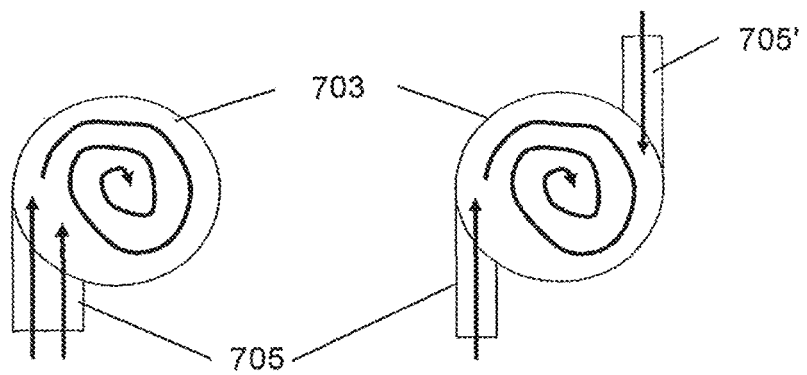

FIGS. 7*a* to 7*c* show a sixth embodiment of the smoking system. FIG. 7*a* shows a cross sectional view of the mouthpiece end of the sixth embodiment of the smoking system 700. In FIG. 7*a*, the smoking system 700 includes guides for channelling the air flow within the smoking system. In this embodiment, the guides are provided by removable insert 701 and by the housing walls 703. The air flow is shown by the dotted arrows.

The removable insert 701 is similar to removable insert 601 shown in FIGS. 6*a* to 6*e* and extends only across the center of the smoking system 700, thereby directing the air flow between the air inlet and the capillary wick and heating coil to the outer circumference of the device. In FIG. 7*a*, the liquid cartridge, the capillary wick and the heating coil all form part of the removable insert 701, although this need not be the case.

In addition, the housing inside walls 703 provide guides for channelling the aerosol flow onto the capillary wick and heating coil, and between the capillary wick and heating coil and the air outlet. The housing inside walls 703 also define the aerosol forming chamber 702. In this embodiment, the housing walls 703 are shaped so that the incoming air flow onto the capillary wick and heating coil is directed in an upstream channel 705 tangential to the circular cross section of the device and the circular cross section of the aerosol forming chamber 702.

FIG. 7*b* is a cross section along line D-D of FIG. 7*a*. In FIG. 7*a* the housing inside walls 703 are shaped so that the channel 705 provides an air flow towards the capillary wick and heating coil that is in the tangential direction. This produces a spiralling air flow around the capillary wick and heating coil towards the air outlet.

FIG. 7*c* is a cross section also along line D-D showing an alternative arrangement, in which two channels 705, 705' towards the capillary wick and heating coil are provided. Both channels direct the air flow in a tangential direction and together they produce a spiralling air flow around the capillary wick and heating coil towards the air outlet. Additional tangential upstream channels could also be provided.

The embodiment shown in FIGS. 7*a*, 7*b* and 7*c* provides a substantially tangentially directed air flow onto the capillary wick and heating coil and a substantially spiralling air flow around the capillary wick and heating coil and from the capillary wick and heating coil to the air outlet. It has been found that managing the air flow in this way improves the aerosol formation occurring within the smoking system. The shaped inside walls 703 of the housing, together with the insert 701 direct the air flow so as to supply cool and non-saturated air to the capillary wick and heating coil. Once air flow targets the capillary wick and heating coil, it is immediately evacuated towards the air outlet. This decreases the particle size of the aerosol inhaled by a user. The spiralling air flow around the capillary wick and heating coil increases turbulence and reduces aerosol particle size. The size of the tangential channel or channels and its position relative to the longitudinal axis of the device influence the air flow around the capillary wick and heating coil and therefore the aerosol characteristics. In addition, the centrifugal forces in the spiralling air flow may allow larger aerosol particles to impact and be trapped on the outer walls of the aerosol forming chamber 702. This is shown schematically in FIG. 7*a*. The arrangement of FIG. 7*c* further improves aerosol formation by providing a better flow distribution within the aerosol forming chamber.

A number of variations are possible in the smoking system of FIGS. 7*a*, 7*b* and 7*c*. The cross section of the device is preferably circular, so that the channel 705 can define a tangential air flow. However, other cross sectional shapes are also possible, as long as some sort of upstream tangential channel can be defined. More than one air inlet (in the housing) may be provided. The guides upstream of the capillary wick and heating coil may be formed as one or more removable portions or alternatively as an integral part of the housing or as a combination of both (removable insert 701 combined with shaped housing walls 703, as shown). Similarly, the guides downstream of the capillary wick and heating coil may be formed as one or more removable portions or alternatively as an integral part of the housing (shaped housing inside walls 703, as shown) or as a combination of both. The insert 701 is shown without channels, although longitudinal channels towards the outside of the insert 701 may be provided. In addition, if channels are provided, the insert may extend across the entire cross section of the housing. Any configuration of channels may be provided. The channels may be twisted around the axis of the housing, so as to encourage a swirled airflow. Any channels in insert 701 may be formed by machining. Alternatively, the insert may be formed with channels or holes already formed, by injection molding. The insert 701 may include a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example. The housing inside walls 703 may be shaped appropriately for the desired volume and shape of the aerosol forming chamber within the smoking system. This affects the spiralling aerosol flow around the capillary wick and heating coil and therefore the aerosol characteristics. The tangential channels 705, 705' may be positioned at any height along the capillary wick and may have any suitable cross section.

FIGS. 8a to 8c show a seventh embodiment of the smoking system. FIG. 8a shows a cross sectional view of the mouthpiece end of the seventh embodiment of the smoking system 800. In FIG. 8a, the smoking system 800 includes guides for channelling the air flow within the smoking system. In this embodiment, the guides are provided by removable insert 801, in the shaped housing walls 803 and by impactor 807. The air flow is shown by the dotted arrows.

The removable insert 801 is similar to removable insert 601 shown in FIGS. 6a to 6e and removable insert 701 shown in FIG. 7a and extends only across the center of the smoking system 800, thereby directing the air flow between the air inlet and the capillary wick and heating coil to the outer circumference of the device. In FIG. 8a, the liquid cartridge, the capillary wick and the heating coil all form part of the removable insert 801, although this need not be the case.

In addition, the housing inside walls 803 provide guides for channelling the air flow onto the capillary wick and heating coil. In this embodiment, the housing walls 803 are shaped so that the incoming air flow onto the capillary wick and heating coil is directed through an upstream channel 805 tangential to the circular cross section of the device and the circular cross section of the aerosol forming chamber 802.

In addition, an impactor 807 is provided at the downstream end of the capillary wick and heating coil. The impactor provides guides for channelling the air flow away from the capillary wick and heating coil and towards the air outlet. The impactor 807, in conjunction with the housing inside walls, also defines the aerosol forming chamber 802. The air flow is directed away from the capillary wick and heating coil in the radial direction in downstream channels 809, that is to say, substantially perpendicular to the longitudinal axis of the housing. The impactor 807 allows larger aerosol particles to be trapped on its upstream side. This is shown schematically in FIG. 8a. The housing inside walls 803 may be tapered to direct the air flow towards the air outlet, although this is not shown in FIG. 8a.

FIG. 8b is a cross section along line E-E of FIG. 8a showing the upstream channel 805. The housing walls 803 are shaped so that the channel 805 provides an air flow towards the capillary wick and heating coil that is in the tangential direction. This produces a spiralling air flow around the capillary wick and heating coil.

FIG. 8c is a cross section along line F-F of FIG. 8a showing the downstream channels 809. The impactor 807 and housing walls 803 cooperate so that the channels 809 provide an air flow away from the capillary wick and heating coil that is in substantially the radial direction. That is to say, downstream of the spiralling air flow around the capillary wick and heating coil, the aerosol flow is directed in the radial direction and then towards the air outlet.

The embodiment shown in FIGS. 8a, 8b and 8c provides a substantially tangentially directed air flow onto the capillary wick and heating coil, a substantially spiralling air flow around the capillary wick and heating coil and a substantially radially directed air flow away from the capillary wick and heating coil to the air outlet. It has been found that managing the air flow in this way improves the aerosol formation occurring within the smoking system. The shaped inside walls 803 of the housing, together with the insert 801 direct the air flow so as to supply cool and non-saturated air to the capillary wick and heating coil. This decreases the particle size of the aerosol inhaled by a user. The spiralling air flow around the capillary wick and heating coil increases turbulence and reduces aerosol particle size. Larger aerosol particles may also become trapped on the inside walls of the aerosol forming chamber 802 due to centrifugal forces. This is shown schematically in FIG. 8a. The radially directed outgoing air flow means that once air flow targets the capillary wick and heating coil, it is immediately evacuated towards the air outlet. Additional upstream tangential channels may be provided (as in FIG. 7c for example) which may provide a better flow distribution within the aerosol forming chamber. The size of the tangential channel or channels and its position relative to the longitudinal axis of the device influence the air flow around the capillary wick and heating coil and therefore the aerosol characteristics. In addition, the impactor may allow larger aerosol particles to impact on its upstream wall. This is shown schematically in FIG. 8a.

A number of variations are possible in the smoking system of FIGS. 8a, 8b and 8c. The cross section of the device is preferably circular, so that the channel 805 can define a tangential air flow. However, other cross sectional shapes are also possible, as long as an upstream tangential channel can be defined. More than one air inlet (in the housing) may be provided. The guides upstream of the capillary wick and heating coil may be formed as one or more removable portions or alternatively as an integral part of the housing or as a combination of both (removable insert 801 combined with shaped housing walls 803, as shown). Similarly, the guides downstream of the capillary wick and heating coil may be formed as one or more removable portions or alternatively as an integral part of the housing or as a combination of both (shaped housing inside walls 803 combined with impactor 807, as shown). The insert 801 is shown without channels, although longitudinal channels towards the outside of the insert 801 may be provided.

In addition, if channels are provided, the insert may extend across the entire cross section of the housing. Any configuration of channels may be provided. The channels may be twisted around the axis of the housing, so as to encourage a swirled airflow. Any channels in insert 801 may be formed by machining. Alternatively, the insert may be formed with channels or holes already formed, by injection molding. The insert 801 may include a locating pin or protrusion (not shown) on its outer surface for cooperating with a recess (also not shown) on the inside of the housing walls, so as to ensure that the insert is correctly positioned within the smoking system. This is important for the electrical connections to the heating coil, for example. The housing inside walls 803 may be shaped appropriately for the desired volume and shape of the aerosol forming chamber within the smoking system. This affects the spiralling aerosol flow around the capillary wick and heating coil and therefore the aerosol characteristics. The tangential channel 805 may be positioned at any height along the capillary wick and may have any suitable cross section. Any number of radial channels 809 may be provided. The impactor 807 may be formed with any appropriate shape and is preferably designed in conjunction with the shaped housing inside walls 803, in order to channel the air flow as desired.

Figure 9A:
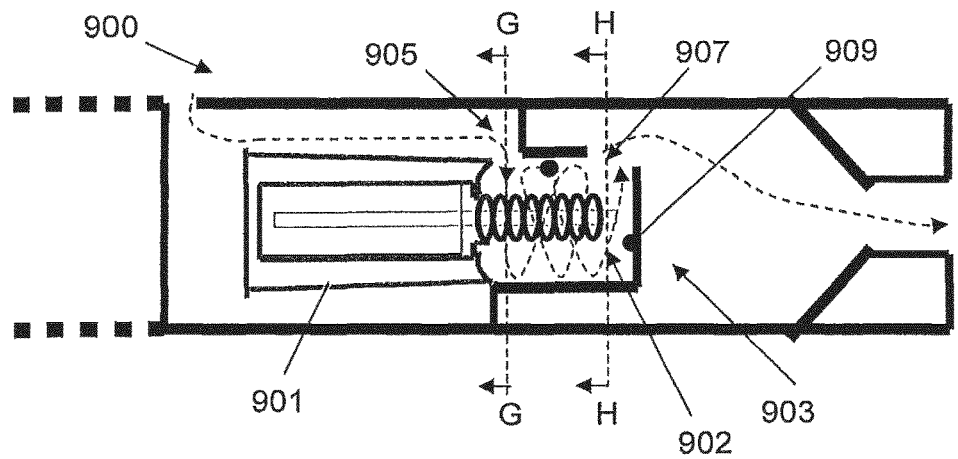
FIGS. 9a, 9b, 9c and 9d show an eighth embodiment of the smoking system.

FIGS. 9a to 9d show an eighth embodiment of the smoking system. FIG. 9a shows a cross sectional view of the mouthpiece end of the eighth embodiment of the smoking system 900. In FIG. 9a, the smoking system 900 includes guides for channelling the air flow within the smoking system. In this embodiment, the guides are provided in removable insert 901 and in the shaped housing walls 903. The air flow is shown by the dotted arrows.

The removable insert 901 is similar to removable inserts 601, 701 and 801 and extends only across the center of the smoking system 900, thereby directing the air flow between the air inlet and the capillary wick and heating coil to the outer circumference of the housing. In FIG. 9a, the liquid cartridge, the capillary wick and the heating coil all form part of the removable insert 901, although this need not be the case.

In addition, the housing inside walls 903 provide guides for channelling the aerosol flow onto the capillary wick and heating coil and off the capillary wick and heating coil. In this embodiment, the housing walls 903 are shaped so that the incoming air flow onto the capillary wick and heating coil is directed through an upstream channel 905 tangential to the circular cross section of the housing and the circular cross section of the aerosol forming chamber 902. In addition, the housing walls 903 are shaped so that the outgoing air flow off the capillary wick and heating coil is directed through an downstream channel 907 also tangential to the circular cross section of the housing and the circular cross section of the aerosol forming chamber 902. In addition, the housing walls 903 are shaped to provide an impactor surface 909 downstream of the capillary wick and heating coil. The impactor surface 909 may allow larger aerosol particles to be trapped. This is shown schematically in FIG. 9a. The housing inside walls also define the aerosol forming chamber 902. The housing inside walls 903 may be tapered to direct the air flow towards the air outlet, although this is not shown in FIG. 9a.

Figures 9B, 9C:
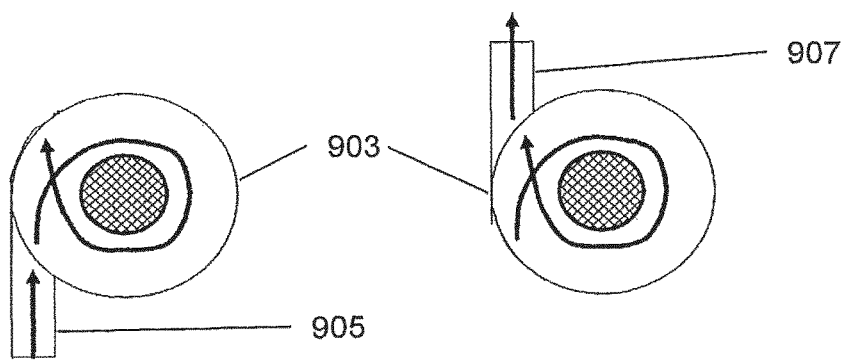

FIG. 9b is a cross section along line G-G of FIG. 9a showing the upstream channel 905. The housing walls 903 are shaped so that the channel 905 provides an air flow towards the capillary wick and heating coil that is in the tangential direction. This produces a spiralling air flow around the capillary wick and heating coil.

FIG. 9c is a cross section along line H-H of FIG. 9a showing the downstream channel 907. The housing walls 903 are shaped so that the channel 907 provides an air flow away from the capillary wick and heating coil that is in the tangential direction. That is to say, after the air has spiralled around the capillary wick and heating coil, it is directed in the tangential direction and then towards the air outlet.

Figure 9D:
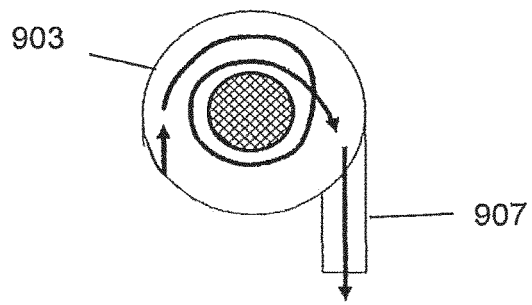

FIG. 9d shows an alternative cross section along line H-H of FIG. 9a, also showing downstream channel 907'. In FIG. 9c, the channel 907 is on the same side of the device as the channel 905. In FIG. 9d, the channel 907' is on the opposite side of the device as the channel 905.

The embodiment shown in FIGS. 9a, 9b, 9c and 9d provides a substantially tangentially directed air flow onto the capillary wick and heating coil, a substantially spiralling air flow around the capillary wick and heating coil and a substantially tangentially directed air flow off the capillary wick and heating coil and then to the air outlet. It has been found that managing the air flow in this way improves the aerosol formation occurring within the smoking system.

The shaped inside walls 903 of the housing, together with the insert 901 direct the air flow so as to supply cool and non-saturated air to the capillary wick and heating coil. This decreases the particle size of the aerosol inhaled by a user. The spiralling air flow around the capillary wick and heating coil increases turbulence and reduces aerosol particle size. Larger aerosol particles may also become trapped on the inside walls of the aerosol forming chamber 902 due to centrifugal forces. This is shown schematically in FIG. 9a. The tangentially directed outgoing air flow means that once air flow has circled the capillary wick and heating coil, it is immediately evacuated towards the air outlet. Additional upstream or downstream tangential channels may be provided which may provide a better flow distribution within the aerosol forming chamber. The size of the tangential channels and their position relative to the longitudinal axis of the device influence the air flow around the capillary wick and heating coil and therefore the aerosol characteristics.

A number of variations are possible in the smoking system of FIGS. 9a, 9b, 9c and 9d. The cross section of the device is preferably circular, so that the channels 905 and 907 can define a tangential air flow. However, other cross sectional shapes are also possible as long as tangential channels can be defined. More than one air inlet (in the housing) may be provided. The guides upstream of the capillary wick and heating coil may be formed as one or more removable portions or alternatively as an integral part of the housing or as a combination of both (removable insert 901 combined with shaped housing walls 903, as shown). Similarly, the guides downstream of the capillary wick and heating coil may be formed as one or more removable portions or alternatively as an integral part of the housing (shaped housing walls 903, as shown) or as a combination of both.

Moreover, the insert 901 is shown without channels, although longitudinal channels towards the outside of the insert 901 may be provided. In addition, if channels are provided, the insert may extend across the entire cross section of the housing. Any configuration of channels may be provided. The channels may be twisted around the axis of the housing, so as to encourage a swirled airflow. Any channels in insert 901 may be formed by machining. Alternatively, the insert may be formed with channels or holes already formed, by injection molding. The insert 901 may include a locating pin or protrusion (not shown) on its outer surface for cooperating with a recess (also not shown) on the inside of the housing walls, so as to ensure that the insert is correctly positioned within the smoking system. This is important for the electrical connections to the heating coil, for example. The housing inside walls 903 may be shaped appropriately for the desired volume and shape of the aerosol forming chamber within the smoking system. This affects the spiralling aerosol flow around the capillary wick and heating coil and therefore the aerosol characteristics. The tangential channels 905, 907 may be positioned at any height along the capillary wick and may have any suitable cross section. Any number of tangential upstream and downstream channels may be provided.

Figure 10A:
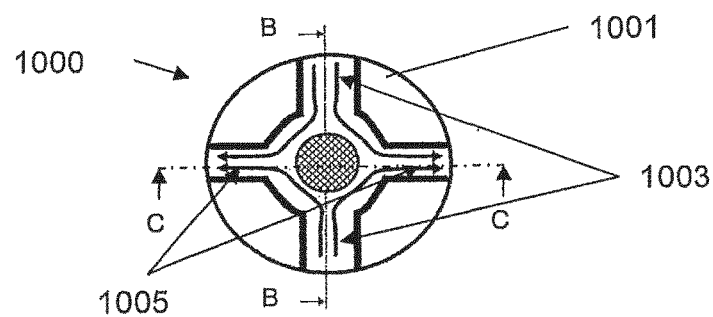
FIGS. 10a, 10b, 10c and 10d show a ninth embodiment of the smoking system.
Figure 10B:
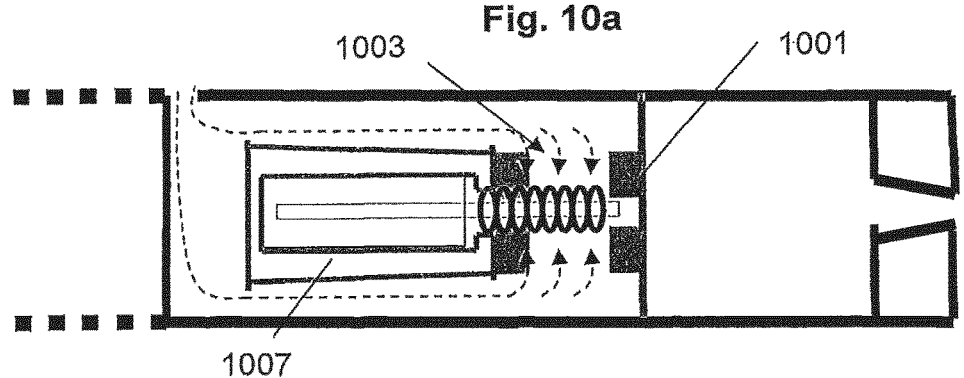
Figure 10C:
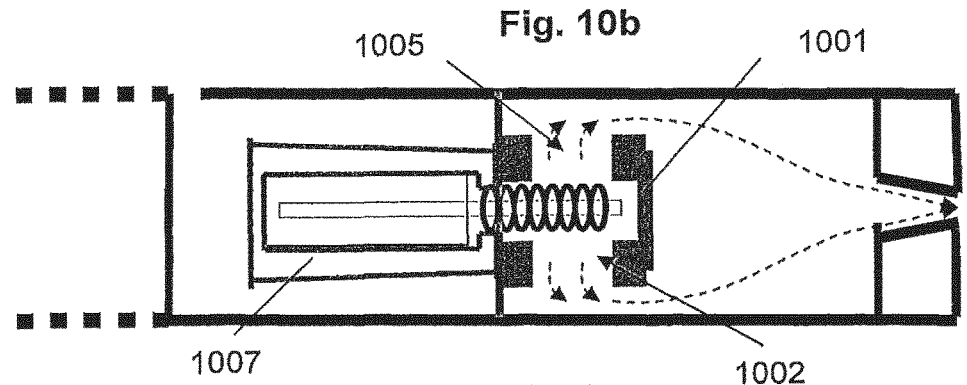

FIGS. 10a to 10d show a ninth embodiment of the smoking system. FIG. 10a shows a cross sectional view of the smoking system including removable insert 1001. FIG. 10b is a cross section along line B-B of FIG. 10a, showing the mouthpiece end only. FIG. 10c is a cross section along line C-C of FIG. 10a, showing the mouthpiece end only. In FIGS. 10a, 10b and 10c, the smoking system 1000 includes guides for channelling the air flow within the smoking system. The air flow is shown by the dotted arrows.

The removable insert 1001 is shown in cross section in FIG. 10*a*. The insert includes upstream channels 1003 for channelling the air flow from the air inlet onto the capillary wick and heating coil and downstream channels 1005 for channelling the air flow away from the capillary wick and heating coil towards the air outlet. The channels 1003 and 1005 are substantially perpendicular to one another and also substantially perpendicular to the longitudinal axis of the housing.

FIG. 10*b* shows across section along B-B of FIG. 10*a* and FIG. 10*c* shows a cross section along C-C of FIG. 10*a*. As seen in FIGS. 10*b* and 10*c*, in this embodiment, the guides are provided by removable insert 1001 and removable insert 1007. The removable insert 1007 is similar to removable inserts 601, 701, 801 and 901 and extends only across the center of the smoking system 1000, thereby directing the air flow between the air inlet and the capillary wick and heating coil to the outer circumference of the housing. In FIGS. 10*b* and 10*c*, the liquid cartridge, the capillary wick and the heating coil all form part of the removable insert 1007, although this need not be the case. The removable insert 1001 is positioned around the capillary wick and heating coil. The removable insert 1001 extends across the entire cross section of the device.

Because FIG. 10*b* shows across section along B-B of FIG. 10*a*, FIG. 10*b* shows the air flow upstream of the capillary wick and heating coil. As shown in FIGS. 10*a* and 10*b*, the channels 1003 direct the air flow onto the capillary wick and heating coil in a substantially radial direction, that is to say, substantially perpendicular to the longitudinal axis of the housing.

Because FIG. 10*c* shows across section along C-C of FIG. 10*a*, FIG. 10*c* shows the air flow downstream of the capillary wick and heating coil. As shown in FIGS. 10*a* and 10*c*, the channels 1005 direct the air flow away from the capillary wick and heating coil in a substantially radial direction. In addition, the channels 1005 define the aerosol forming chamber 1002.

The housing walls may additionally be tapered towards the air outlet, although this is not shown in FIGS. 10*b* and 10*c*.

Figure 10D:
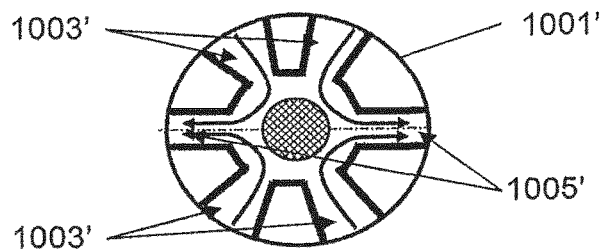

FIG. 10*d* shows an alternative arrangement for the removable insert 1001'. In this embodiment, the insert includes four upstream channels 1003' for channelling the air flow from the air inlet onto the capillary wick and heating coil. As in FIG. 10*a*, the insert also includes two downstream channels 1005' for channelling the air flow away from the capillary wick and heating coil towards the air outlet. The channels 1003' and 1005' are substantially perpendicular to the longitudinal axis of the housing. The channels are directed in the radial direction. Although two upstream channels 1003 are shown in FIG. 10*a* and four upstream channels 1003' are shown in FIG. 10*d*, any suitable number of upstream channels may be provided, all in the radial direction and substantially perpendicular to the longitudinal axis of the housing. Similarly, although two downstream channels 1005, 1005' are shown in FIGS. 10*a* and 10*d*, any suitable number of downstream channels may be provided, all in the radial direction and substantially perpendicular to the longitudinal axis of the housing.

The embodiments shown in FIGS. 10*a* to 10*d* provide a substantially radially directed air flow onto the capillary wick and heating coil and a substantially radially directed air flow off the capillary wick and heating coil. It has been found that managing air flow in this way improves the aerosol formation occurring within the smoking system. The guides provided by the inserts 1007 and 1001 channel the air flow as to direct the air flow onto the capillary wick and heating coil in a substantially radial direction. This provides the capillary wick and heating coil with cool, non-saturated air, which decreases the particle size of the aerosol inhaled by a user. The guides provided by the insert 1001 channel the air flow as to direct the air flow off the capillary wick and heating coil in a substantially radial direction and also reduce the volume of the aerosol forming chamber 1002 in the smoking system. This improves aerosol flow towards the air outlet. This improves the smoking experience.

A number of variations are possible in the smoking system of FIGS. 10*a* to 10*d*. First, although the cross section of the device is shown as circular in FIGS. 10*a* to 10*d*, this need not be the case. Second, more than one air inlet may be provided. The guides upstream of the capillary wick and heating coil may be formed as one or more removable portions (inserts 1001 and 1007, as shown) or alternatively as an integral part of the housing or as a combination of both. Similarly, the guides downstream of the capillary wick and heating coil may be formed as one or more removable portions (insert 1001, as shown) or alternatively as an integral part of the housing or as a combination of both. The insert 1007 is shown without channels, although longitudinal channels towards the outside of the insert may be provided.

In addition, if channels are provided, the insert may extend across the entire cross section of the housing. Any configuration of channels may be provided. The channels may be twisted around the axis of the housing, so as to encourage a swirled airflow. The channels in insert 1007 may be formed by machining. Alternatively, the insert may be formed with channels or holes already formed, by injection molding. Preferably, the insert 1007 includes a locating pin or protrusion (not shown) on its outer surface for cooperating with a recess (also not shown) on the inside of the housing walls, so as to ensure that the insert is correctly positioned within the smoking system. This is important for the electrical connections to the heating coil, for example.

Any suitable configuration of channels may be provided in insert 1001. The channels may be evenly or non-evenly distributed circumferentially around the insert. The channels may have a constant cross sectional shape and area along their length, or the cross sectional shape can vary along the length. The channels may include some channels having different cross sectional shapes and areas from others. The channels in insert 1001 may be formed by machining. Alternatively, the insert may be formed with channels or holes already formed, by injection molding. Preferably, the insert 1001 includes a locating pin or protrusion (not shown) on its outer surface for cooperating with a recess (also not shown) on the inside of the housing walls, so as to ensure that the insert is correctly positioned within the smoking system. This is important for the electrical connections to the heating coil, for example. The channels 1005 may be shaped appropriately for the desired volume and shape of the aerosol forming chamber within the smoking system.

Figure 11A:
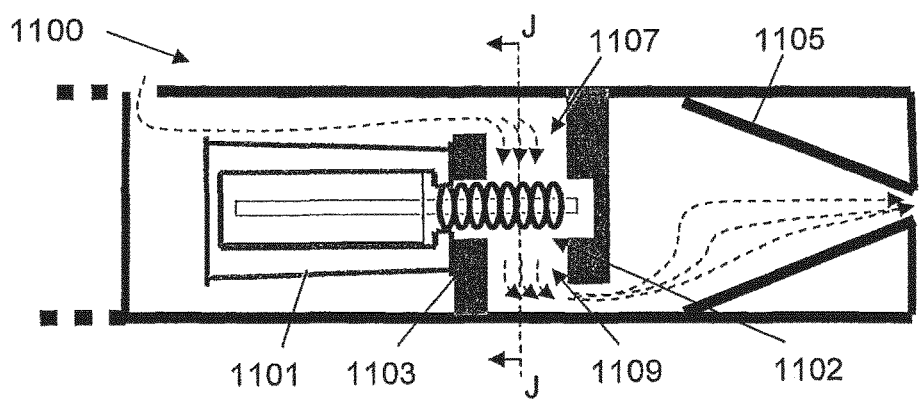
FIGS. 11a to 11l show a tenth embodiment of the smoking system.

FIGS. 11*a* to 11*n* show a tenth embodiment of the smoking system. In each of FIGS. 11*a* to 11 *n*, the smoking system includes guides for channelling the air flow within the smoking system. The air flow is shown by the dotted arrows.

Figure 11B:
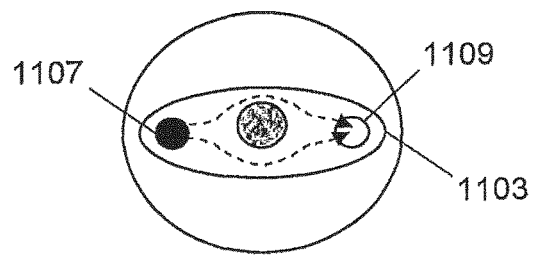

FIG. 11*a* shows a first arrangement of the smoking system 1100, and FIG. 11*b* is a cross section along line J-J of FIG. 11*a*. In FIGS. 11*a* and 11*b*, the guides are provided by removable insert 1101, second removable insert 1103 and by the shaped housing inside walls 1105. The removable insert 1101 extends only across the center of the smoking system

1100, thereby directing the air flow between the air inlet and the capillary wick and heating coil to the outer circumference of the housing. In FIG. 11a, the liquid cartridge, the capillary wick and the heating coil all form part of the removable insert 1101, although this need not be the case.

Preferably, the second removable insert 1103 is shaped so that the air flow is directed across the capillary wick and heating coil in a substantially perpendicular direction. That is to say, the air flow is substantially perpendicular to the longitudinal axis of the housing and to the capillary wick. The second removable insert 1103 provides an upstream channel 1107 on one side of the insert and an downstream channel 1109 on the other side of the insert. When the insert is positioned around the capillary wick and heating coil, the air therefore flows directly across the capillary wick and heating coil. The insert 1103 also defines the aerosol forming chamber 1102.

In addition, the housing inside walls 1005 provide guides for channelling the air and aerosol flow between the capillary wick and heating coil and the air outlet. In this embodiment, the housing inside walls 1105 are tapered towards the air outlet so as to direct the air and aerosol flow towards the air outlet.

Figure 11C:
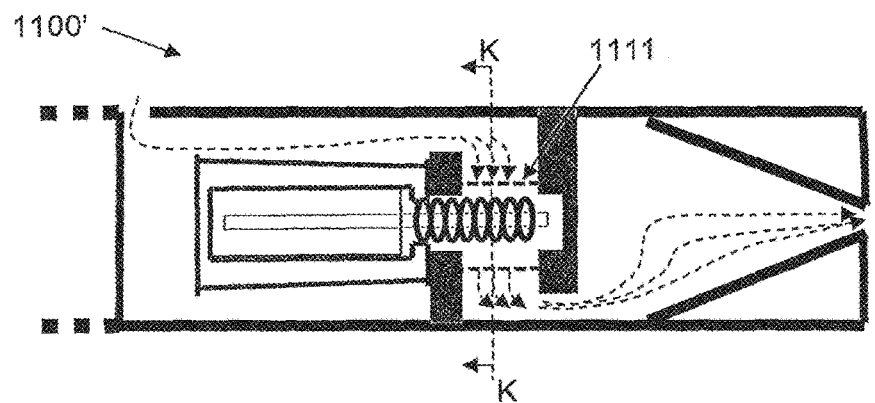
Figure 11D:
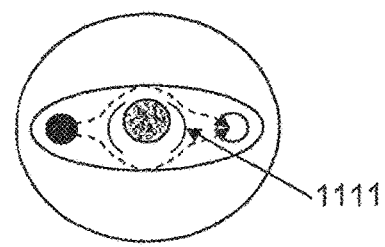

FIG. 11c shows a second arrangement of the smoking system 1100' and FIG. 11d is a cross section along line K-K of FIG. 11c. The arrangement shown in FIGS. 11c and 11d is identical to that shown in FIGS. 11a and 11b except that second removable insert 1103 includes a perturbator 1111 surrounding the capillary wick and heating coil. In this embodiment, the perturbator 1111 includes a cylindrical tube surrounding the capillary wick and heating coil, with holes to direct the air flow onto and away from the capillary wick and heating coil. This provides additional turbulence in the aerosol forming chamber 1102.

Figure 11E:
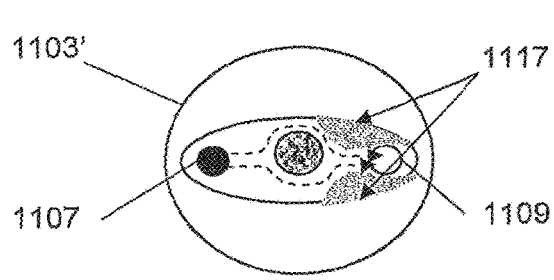

FIG. 11e shows another embodiment of removable insert 1103'. The embodiment shown in FIG. 11e is identical to that shown in FIG. 11b except that the aerosol forming chamber is formed with restrictions 1117 towards the downstream side. The restrictions 1117 provide turbulence and, in particular, allow the air flow to strike the downstream side of the capillary wick and heating coil.

Figure 11F:
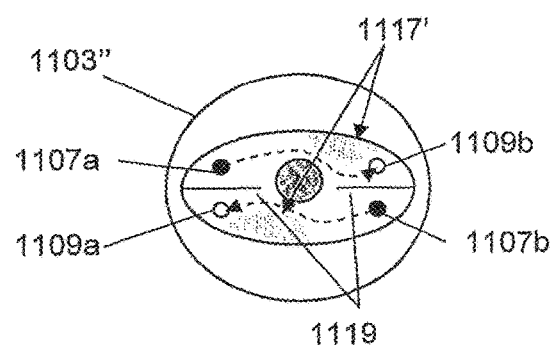

FIG. 11f shows another embodiment of removable insert 1103". The embodiment shown in FIG. 11f provides two upstream channels 1107a and 1107b on opposite sides of the insert and two downstream channels 1109a and 1109b on opposite sides of the insert. Air flow is directed from upstream channel 1107a, directly across the capillary wick and heating coil, towards downstream channel 1109b. At the same time, air flow is directed in the opposite direction from upstream channel 1107b, directly across the capillary wick and heating coil, towards downstream channel 1109a. This provides additional turbulence. In FIG. 11f, the aerosol forming chamber is formed with divisions 1119. This prevents or reduces flow from upstream channel 1107a to downstream channel 1109a and from upstream channel 1107b to downstream channel 1109b. In FIG. 11f, the aerosol forming chamber is formed with restrictions 1117' towards each downstream side, although the restrictions 1117' may be omitted. The restrictions 1117' provide turbulence and, in particular, allow the air flow to strike the downstream side of the capillary wick and heating coil.

Figure 11G:
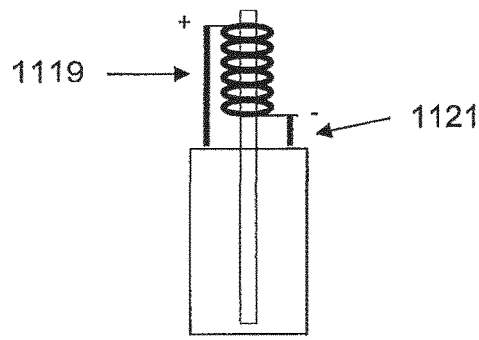
Figure 11H:
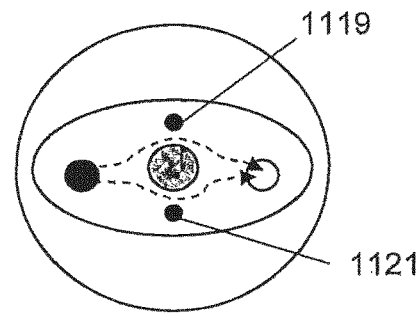

FIG. 11g shows another arrangement of the smoking system. In FIG. 11g, only the liquid cartridge, the capillary wick and the heating coil are shown for clarity. FIG. 11h is a cross section, similar to the cross sections in FIGS. 11b, 11d, 11e and 11f, but showing the FIG. 11g arrangement. In FIGS. 11g and 11h, two pins 1119, 1121 are provided in the air flow across the capillary wick and heating coil. The pins direct the air flow and provide further turbulence in the aerosol forming chamber. In the embodiment shown in FIGS. 11g and 11h, the pins are the connection pins for the heating coil, pin 1119 being the positive connection, pin 1121 being the negative connection. However, this need not be the case.

Figure 11I:
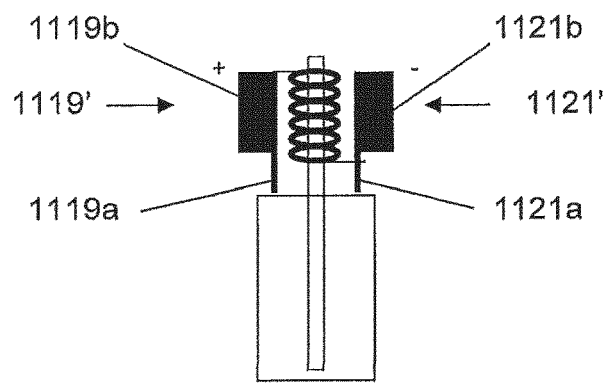
Figure 11J:
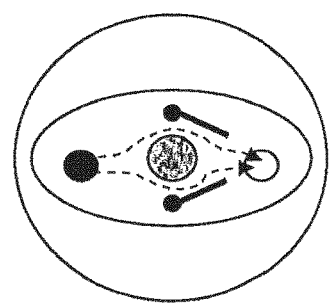

FIG. 11i shows an alternative version for the arrangement shown in FIG. 11g. In FIG. 11i, the pins 1119', 1121' are formed as flags. Pin 1119' has a pin portion 1119a at its base and a wider blade portion 1119b at its upper part. Similarly, pin 1121' has a pin portion 1121a at its base and a wider blade portion 1121b at its upper part. This provides better direction of the air flow across the capillary wick and heating coil. FIG. 11j shows another alternative version for the arrangement shown in FIG. 11g. In FIG. 11j, the pins are formed as wide heating blades 1119", 1121". Again, this provides better direction of the air flow across the capillary wick and heating coil.

Figure 11K:
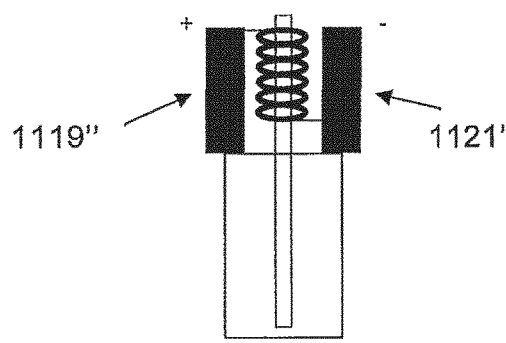
Figure 11L:
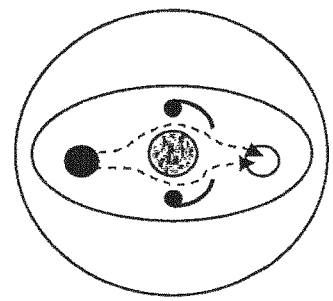

FIGS. 11k and 11l show two alternative arrangements for the pins shown in FIGS. 11i and 11j. FIG. 11k is a cross section, similar to the cross sections in FIGS. 11b, 11d, 11e, 11f and 11h. As shown in FIG. 11k, the blade portions of the pins may be straight and directed in the downstream direction, that is to say, towards the downstream channel 1109. FIG. 11l is a cross section, similar to the cross sections in FIGS. 11b, 11d, 11e, 11f, 11h and 11k. As shown in FIG. 11l, the blade portions of the pins may be curved and directed in the downstream direction, that is to say, towards the downstream channel 1109.

The embodiments shown in FIGS. 11a to 11l provide a substantially radially directed air flow onto the capillary wick and heating coil and a substantially radially directed air flow off the capillary wick and heating coil. In particular, the air flow is directed across the capillary wick and heating coil. It has been found that managing air flow in this way improves the aerosol formation occurring within the smoking system. The guides provided by the inserts 1101 and 1103 channel the air flow as to direct the air flow onto the capillary wick and heating coil in a substantially radial direction. This provides the capillary wick and heating coil with cool, non-saturated air, which decreases the particle size of the aerosol inhaled by a user. The guides provided by the insert 1103 channel the air flow as to direct the air flow off the capillary wick and heating coil in a substantially radial direction and also reduce the volume of the aerosol forming chamber in the smoking system. This improves aerosol flow towards the air outlet. In addition, in the air flow, additional components may be provided to increase turbulence. This improves the smoking experience.

A number of variations are possible in the smoking system of FIGS. 11a to 11l. First, although the cross section of the device is shown as circular in FIGS. 11a to 11l, this need not be the case. Second, more than one air inlet may be provided. The guides upstream of the capillary wick and heating coil may be formed as one or more removable portions (inserts 1101 and 1103, as shown) or alternatively as an integral part of the housing or as a combination of both. Similarly, the guides downstream of the capillary wick and heating coil may be formed as one or more removable portions or alternatively as an integral part of the housing or as a combination of both (insert 1103 and shaped housing walls 1105, as shown). The insert 1101 is shown without channels, although longitudinal channels towards the outside of the insert may be provided. In addition, if channels are provided, the insert may extend across the entire cross section of the housing. Any configuration of channels may be provided. The channels may be twisted around the axis of the housing, so as to encourage a swirled airflow. The channels in insert 1101 may be formed by machining. Alternatively, the insert may be formed with channels or holes already formed, by injection molding. Preferably, the insert 1101 includes a locating pin or protrusion (not shown) on its outer surface for cooperating with a recess (also not shown) on the inside of the housing walls, so as to ensure that the insert is correctly positioned within the smoking system. This may be important for the electrical connections to the heating coil, for example.

Any suitable configuration of channels may be provided in insert 1103 including any suitable number of upstream channels and any suitable number of downstream channels. The channels may have a constant cross sectional shape and area along their length, or the cross sectional shape can vary along the length. The channels may include some channels having different cross sectional shapes and areas from others. The channels in insert 1103 may be formed by machining. Alternatively, the insert may be formed with channels or holes already formed, by injection molding. Preferably, the insert 1103 includes a locating pin or protrusion (not shown) on its outer surface for cooperating with a recess (also not shown) on the inside of the housing walls, so as to ensure that the insert is correctly positioned within the smoking system. The insert 1103 may be shaped appropriately for the desired volume of the aerosol forming chamber within the smoking system.

The pins shown in FIGS. 11g to 11l may have suitable shape in order to direct the air flow across the capillary wick and heating element as desired. In addition, although the pins are shown as the connections to the heating coil, this need not be the case.

A large number of embodiments have been described and it should be understood that features described in relation to one embodiment may also apply to another embodiment, where appropriate. The scope of the present invention is defined with reference to the following claims.

In this specification, the word "about" is often used in connection with numerical values to indicate that mathematical precision of such values is not intended. Accordingly, it is intended that where "about" is used with a numerical value, a tolerance of ±10% is contemplated for that numerical value.

In this specification the words "generally" and "substantially" are sometimes used with respect to terms. When used with geometric terms, the words "generally" and "substantially" are intended to encompass not only features which meet the strict definitions but also features which fairly approximate the strict definitions.

While the foregoing describes in detail a preferred smoking system and methods of making with reference to a specific embodiment thereof, it will be apparent to one skilled in the art that various changes and modifications may be made to the smoking system and equivalents method may be employed, which do not materially depart from the spirit and scope of the invention. Accordingly, all such changes, modifications, and equivalents that fall within the spirit and scope of the invention as defined by the appended claims are intended to be encompassed thereby.

We claim:

1. A system comprising:
   a housing having a mouthpiece end and a body end;
   a storage portion in the housing, the storage portion configured to contain an aerosol-forming material;
   a wick in communication with the storage portion;
   a heater in the housing, the heater configured to heat a portion of the aerosol-forming material;
   a power supply electrically connected to the heater;
   at least one guide configured to channel air flow towards the wick;
   an air outlet at the mouthpiece end;
   an air inlet in fluid communication with the air outlet; and
   a detection system configured to sense a puff,
   wherein the at least one guide comprises a removable insert and a portion of an inside wall of the housing.

2. The system of claim 1, wherein the wick comprises a porous material, a capillary material, or the porous material and the capillary material.

3. The system of claim 1, wherein the removable insert includes the storage portion, the wick, and the heater.

4. The system of claim 1, wherein the removable insert includes at least one channel configured to channel air flow.

5. The system of claim 4, wherein the at least one channel is twisted around an axis of the housing.

6. The system of claim 1, wherein the removable insert includes at least two channels, the at least two channels having different cross-sectional shapes.

7. The system of claim 6, wherein the at least two channels are evenly distributed circumferentially around the removable insert.

8. The system of claim 6, wherein the at least two channels are non-evenly distributed circumferentially around the removable insert.

9. The system of claim 1, wherein the removable insert is a grill insert including a plurality of longitudinally spaced holes.

10. The system of claim 1, wherein the removable insert is a grooved insert including a solid cylindrical tube having a plurality of channels formed in a radial direction.

11. The system of claim 1, wherein the removable insert is a grooved insert including a solid conical tube having a plurality of channels formed in a radial direction.

12. The system of claim 1, wherein the removable insert substantially surrounds the wick and the heater.

13. The system of claim 1, further comprising:
    an impactor in the housing, the impactor configured to reduce a particle size of particles.

14. The system of claim 1, wherein the inside wall of the housing is tapered towards the air inlet.

* * * * *